(12) United States Patent
Jackson

(10) Patent No.: US 12,042,185 B2
(45) Date of Patent: Jul. 23, 2024

(54) PIVOTAL BONE ANCHOR ASSEMBLY WITH RESILIENTLY BIASED FRICTION FIT INSERT

(71) Applicant: Roger P. Jackson, Prairie Village, KS (US)

(72) Inventor: Roger P. Jackson, Prairie Village, KS (US)

( * ) Notice: Subject to any disclaimer, the term of this patent is extended or adjusted under 35 U.S.C. 154(b) by 0 days.

(21) Appl. No.: 18/359,566

(22) Filed: Jul. 26, 2023

(65) Prior Publication Data

US 2023/0363800 A1 Nov. 16, 2023

Related U.S. Application Data

(63) Continuation of application No. 17/033,417, filed on Sep. 25, 2020, now Pat. No. 11,717,328, which is a continuation of application No. 13/068,506, filed on May 12, 2011, now Pat. No. 10,792,074.

(60) Provisional application No. 61/395,692, filed on May 14, 2010.

(51) Int. Cl.
*A61B 17/70* (2006.01)
*A61B 17/86* (2006.01)

(52) U.S. Cl.
CPC ........ *A61B 17/7037* (2013.01); *A61B 17/702* (2013.01); *A61B 17/705* (2013.01); *A61B 17/86* (2013.01)

(58) Field of Classification Search
None
See application file for complete search history.

(56) References Cited

U.S. PATENT DOCUMENTS

| | | | |
|---|---|---|---|
| 5,669,911 A | 9/1997 | Errico et al. |
| 5,672,176 A | 9/1997 | Biedermann et al. |
| 5,690,630 A | 11/1997 | Errico et al. |
| 5,782,833 A | 7/1998 | Haider |
| 5,797,911 A | 8/1998 | Sherman et al. |
| 5,885,286 A | 3/1999 | Sherman et al. |
| 6,010,503 A | 1/2000 | Richelsoph et al. |
| 6,063,090 A | 5/2000 | Schläpfer |

(Continued)

FOREIGN PATENT DOCUMENTS

| | | |
|---|---|---|
| DE | 102013204726 | 9/2014 |
| EP | 1857064 | 11/2007 |
| WO | WO 2009/055747 | 4/2009 |

*Primary Examiner* — Tessa M Matthews
(74) *Attorney, Agent, or Firm* — Polsinelli PC

(57) ABSTRACT

A pivotal bone anchor assembly includes a receiver having a central bore with a seating surface adjacent a bottom opening and a downward-facing surface above the seating surface, and a shank having a head portion positionable within the axial bore. The assembly also includes a compression insert positionable within the central bore above the head portion and having an upper portion with a notch formed therein to define a resiliently compressible structure extending over the notch. When the head portion of the shank and the compression insert are positioned together in the central bore of the receiver, the engagement between the resiliently compressible structure and the downward-facing surface is configured to provide an axially directed resilient biasing force for a pre-lock friction fit of the pivotal bone anchor assembly prior to securing the longitudinal connecting member in the open channel with the closure.

27 Claims, 22 Drawing Sheets

(56) References Cited

U.S. PATENT DOCUMENTS

| | | | |
|---|---|---|---|
| 6,090,111 | A | 7/2000 | Nichols |
| 6,254,602 | B1 | 7/2001 | Justis |
| 6,280,442 | B1 | 8/2001 | Barker et al. |
| 6,355,040 | B1 | 3/2002 | Richelsoph et al. |
| 6,471,705 | B1 | 10/2002 | Biedermann et al. |
| 6,485,491 | B1 | 11/2002 | Farris et al. |
| 6,485,494 | B1 | 11/2002 | Haider |
| 6,540,748 | B2 | 4/2003 | Lombardo |
| 6,565,565 | B1 | 5/2003 | Yuan et al. |
| 6,626,908 | B2 | 9/2003 | Cooper et al. |
| 6,740,086 | B2 | 5/2004 | Richelsoph |
| 6,837,889 | B2 | 1/2005 | Shluzas |
| 6,905,500 | B2 | 6/2005 | Jeon et al. |
| 6,945,975 | B2 | 9/2005 | Dalton |
| 7,066,937 | B2 | 6/2006 | Shluzas |
| 7,087,057 | B2 | 8/2006 | Konieczynski et al. |
| 7,141,051 | B2 | 11/2006 | Janowski et al. |
| 7,144,396 | B2 | 12/2006 | Shluzas |
| 7,163,539 | B2 | 1/2007 | Abdelgany et al. |
| 7,264,621 | B2 | 9/2007 | Coates et al. |
| 7,311,712 | B2 | 12/2007 | Dalton |
| 7,377,923 | B2 | 5/2008 | Purcell et al. |
| 7,445,627 | B2 | 11/2008 | Hawkes et al. |
| 7,604,655 | B2 | 10/2009 | Warnick |
| 7,686,834 | B2 | 3/2010 | Saint Martin |
| 7,686,835 | B2 | 3/2010 | Warnick |
| 7,695,497 | B2 | 4/2010 | Cordaro et al. |
| 7,766,915 | B2 | 8/2010 | Jackson |
| 7,766,945 | B2 | 8/2010 | Nilsson et al. |
| 7,776,067 | B2 | 8/2010 | Jackson |
| 7,789,896 | B2 | 9/2010 | Jackson |
| 7,789,900 | B2 | 9/2010 | Levy et al. |
| 7,811,310 | B2 | 10/2010 | Baker et al. |
| 7,833,251 | B1 | 11/2010 | Ahlgren et al. |
| 7,842,073 | B2 | 11/2010 | Richelsoph et al. |
| 7,901,436 | B2 | 3/2011 | Baccelli |
| 7,909,830 | B2 | 3/2011 | Frigg et al. |
| 7,914,536 | B2 | 3/2011 | MacDonald et al. |
| 7,942,909 | B2 | 5/2011 | Hammill, Sr. et al. |
| 7,947,065 | B2 | 5/2011 | Hammill, Sr. et al. |
| 7,951,173 | B2 | 5/2011 | Hammill, Sr. et al. |
| 7,988,694 | B2 | 8/2011 | Barrus et al. |
| 8,021,397 | B2 | 9/2011 | Farris et al. |
| 8,048,112 | B2 | 11/2011 | Suzuki et al. |
| 8,066,744 | B2 | 11/2011 | Justis et al. |
| 8,075,603 | B2 | 12/2011 | Hammill, Sr. et al. |
| 8,083,776 | B2 | 12/2011 | Alvarez |
| 8,197,517 | B1 | 6/2012 | Lab et al. |
| 8,197,518 | B2 | 6/2012 | Hammill, Sr. et al. |
| 8,221,472 | B2 | 7/2012 | Peterson et al. |
| 8,353,932 | B2 | 1/2013 | Jackson |
| 8,361,123 | B2 | 1/2013 | Fanger et al. |
| 8,382,805 | B2 | 2/2013 | Wang et al. |
| 8,398,683 | B2 | 3/2013 | Berrevoets et al. |
| 8,439,922 | B1 | 5/2013 | Arnold et al. |
| 8,449,578 | B2 | 5/2013 | Keiser et al. |
| 8,556,938 | B2 | 10/2013 | Jackson et al. |
| 8,562,652 | B2 | 10/2013 | Biedermann et al. |
| 8,628,558 | B2 | 1/2014 | Harvey et al. |
| 8,663,290 | B2 | 3/2014 | Doubler et al. |
| 8,663,291 | B2 | 3/2014 | Doubler et al. |
| 8,663,298 | B2 | 3/2014 | Keyer et al. |
| 8,696,712 | B2 | 4/2014 | Biedermann et al. |
| 8,876,869 | B1 | 11/2014 | Schafer et al. |
| 8,882,817 | B2 | 11/2014 | Jones et al. |
| 8,888,827 | B2 | 11/2014 | Harper et al. |
| 8,926,671 | B2 | 1/2015 | Biedermann et al. |
| 8,986,349 | B1 | 3/2015 | German et al. |
| 9,044,272 | B2 | 6/2015 | Shaffrey et al. |
| 9,060,814 | B2 | 6/2015 | Doubler et al. |
| 9,078,705 | B2 | 7/2015 | Matthis et al. |
| 9,119,674 | B2 | 9/2015 | Matthis et al. |
| 9,155,567 | B2 | 10/2015 | Auerbach et al. |
| 9,198,695 | B2 | 12/2015 | Shluzas et al. |
| 9,254,150 | B2 | 2/2016 | Biedermann et al. |
| 9,259,247 | B2 | 2/2016 | Chandanson et al. |
| 9,358,047 | B2 | 6/2016 | Mishra et al. |
| 9,439,680 | B2 | 9/2016 | Biedermann et al. |
| 9,486,246 | B2 | 11/2016 | Biedermann et al. |
| 9,492,204 | B2 | 11/2016 | Biedermann et al. |
| 9,526,529 | B2 | 12/2016 | Charvet |
| 9,572,600 | B2 | 2/2017 | Biedermann et al. |
| 9,649,134 | B2 | 5/2017 | Hannen |
| 9,655,652 | B2 | 5/2017 | Biedermann et al. |
| 9,763,702 | B2 | 9/2017 | Schlaepfer et al. |
| 10,058,354 | B2 | 8/2018 | Jackson et al. |
| 10,064,657 | B2 | 9/2018 | Spitler |
| 10,154,859 | B2 | 12/2018 | Keyer et al. |
| 10,172,647 | B2 | 1/2019 | Elsbury |
| 10,792,074 | B2 | 10/2020 | Jackson |
| 11,234,745 | B2 | 2/2022 | Jackson |
| 2003/0149431 | A1 | 8/2003 | Varieur |
| 2004/0102781 | A1 | 5/2004 | Jeon |
| 2004/0260283 | A1 | 12/2004 | Wu et al. |
| 2005/0203516 | A1 | 9/2005 | Biedermann et al. |
| 2006/0161152 | A1 | 7/2006 | Ensign et al. |
| 2006/0217716 | A1 | 9/2006 | Baker et al. |
| 2007/0118123 | A1 | 5/2007 | Strausbaugh et al. |
| 2007/0270813 | A1 | 11/2007 | Garamszegi |
| 2009/0093844 | A1* | 4/2009 | Jackson ............ A61B 17/7037 606/301 |
| 2010/0087865 | A1* | 4/2010 | Biedermann ...... A61B 17/7046 606/279 |
| 2010/0152787 | A1 | 6/2010 | Walsh et al. |
| 2011/0046683 | A1* | 2/2011 | Biedermann ...... A61B 17/7082 606/305 |
| 2012/0310284 | A1 | 12/2012 | Gerchow |
| 2013/0218213 | A1 | 8/2013 | Lemoine |
| 2014/0025119 | A1 | 1/2014 | Biedermann et al. |

\* cited by examiner

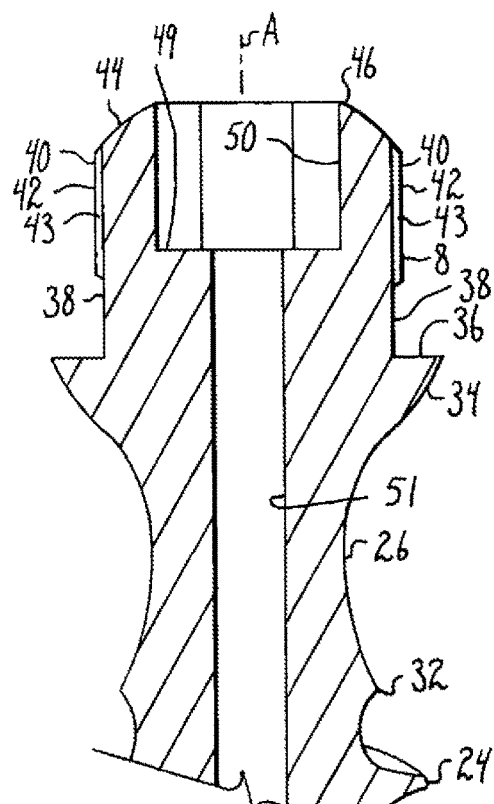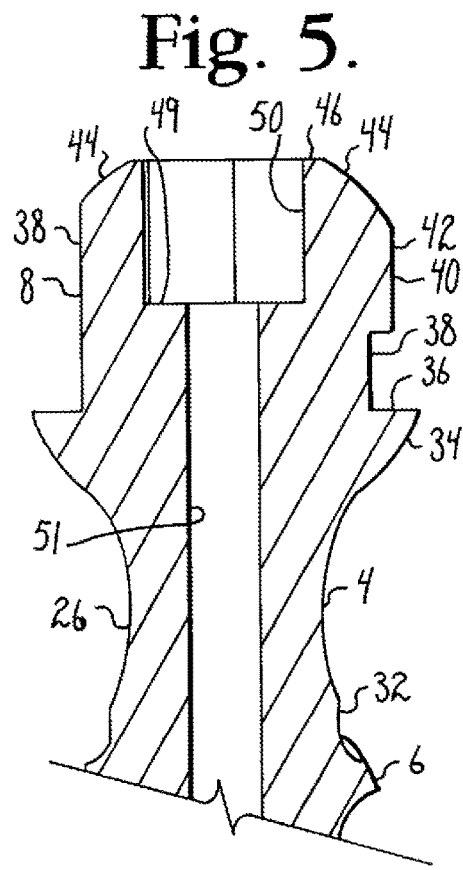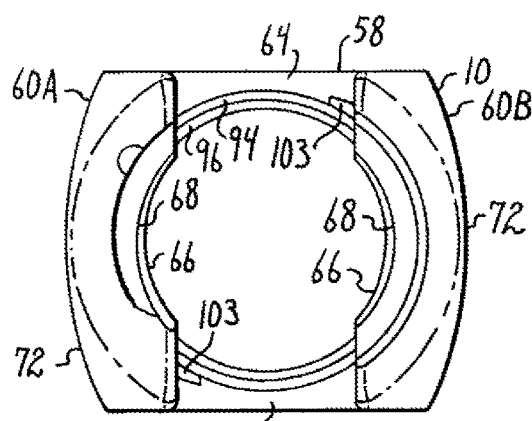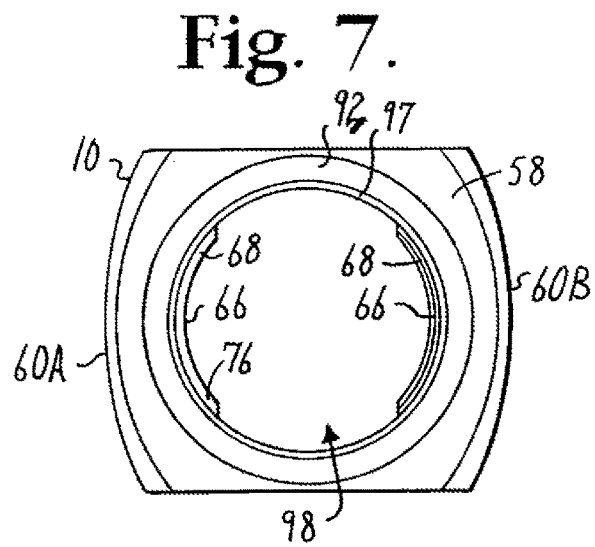

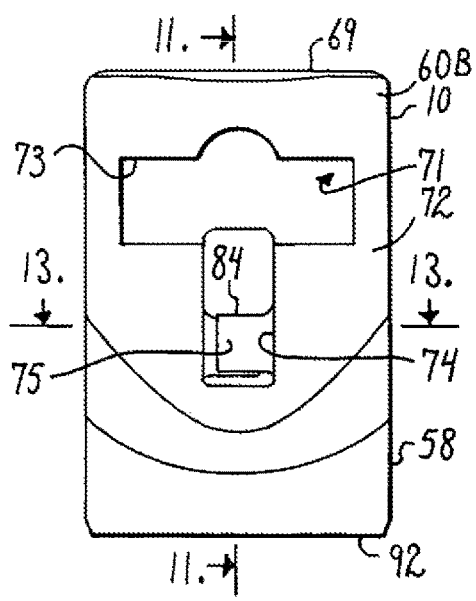
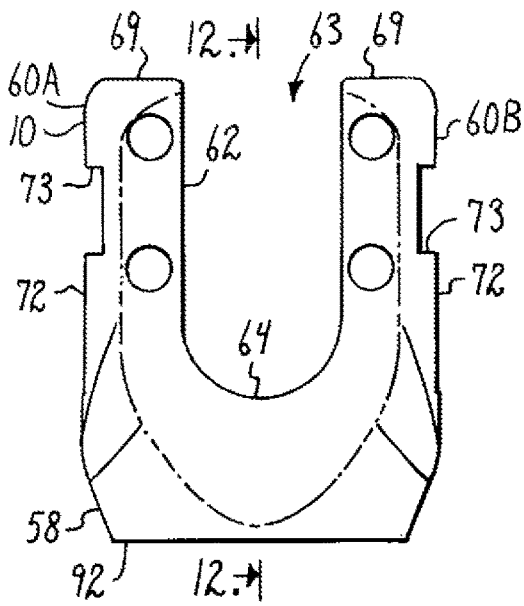
Fig. 8.
Fig. 9.
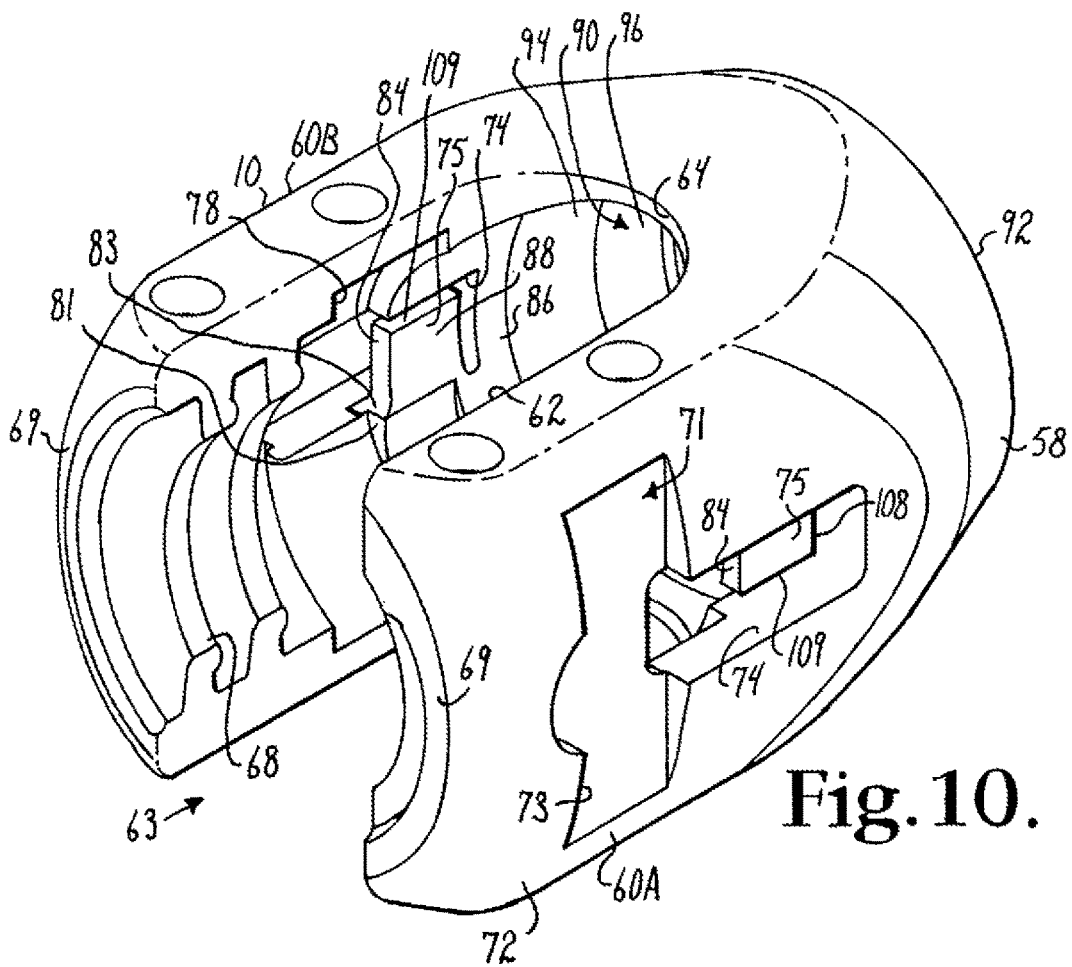
Fig. 10.

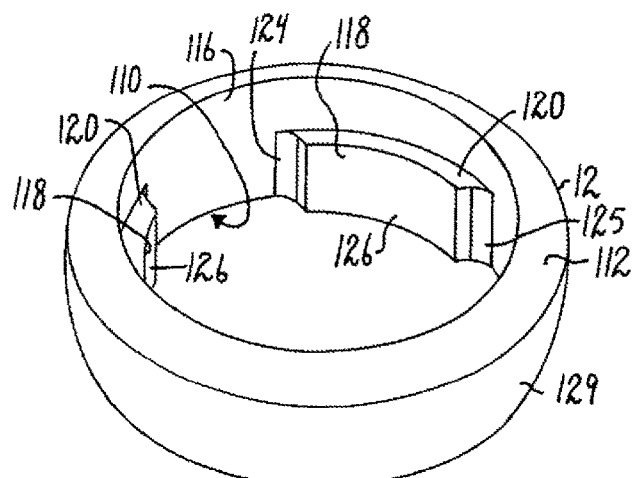
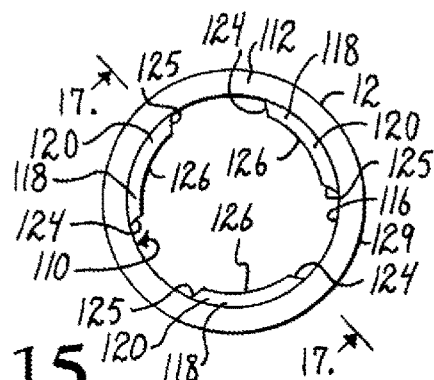
Fig.14.  Fig.15.
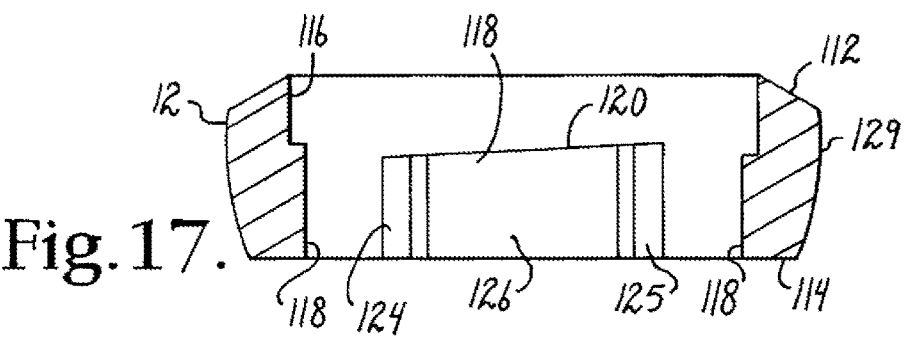
Fig.17.
Fig.18.
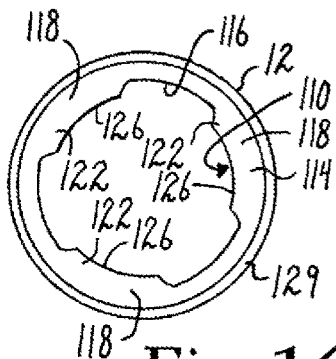
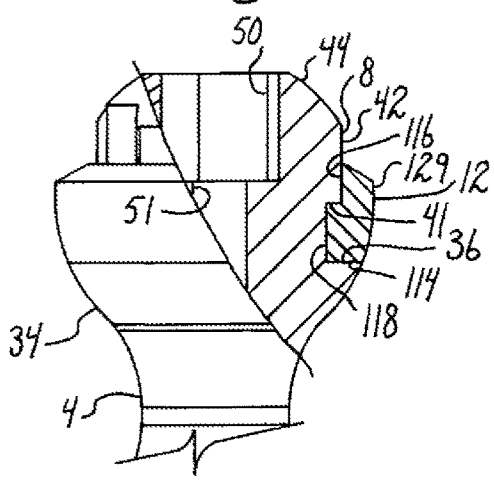
Fig.16.

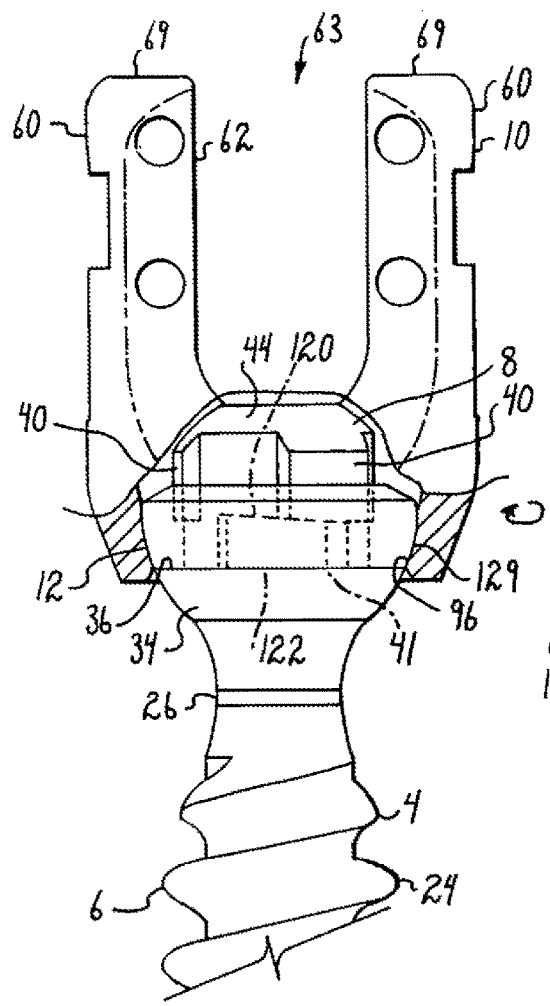
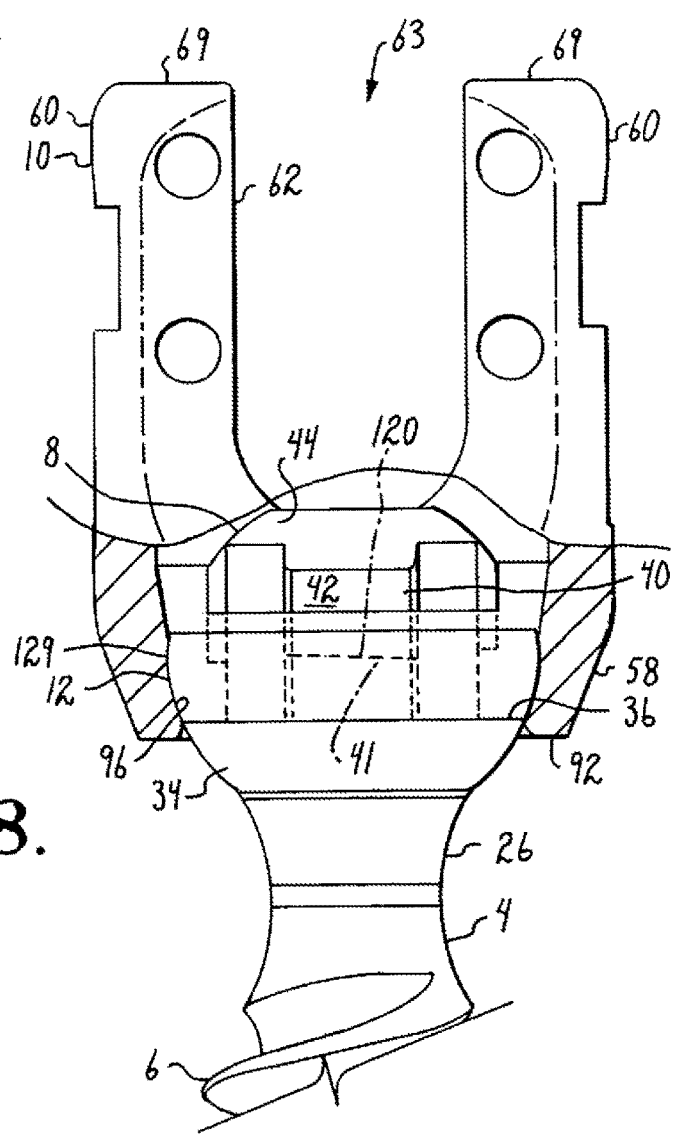

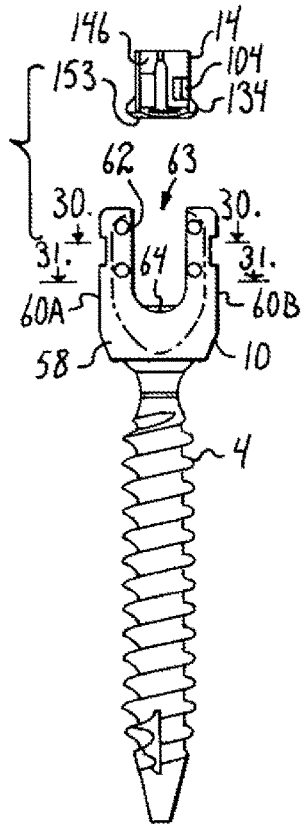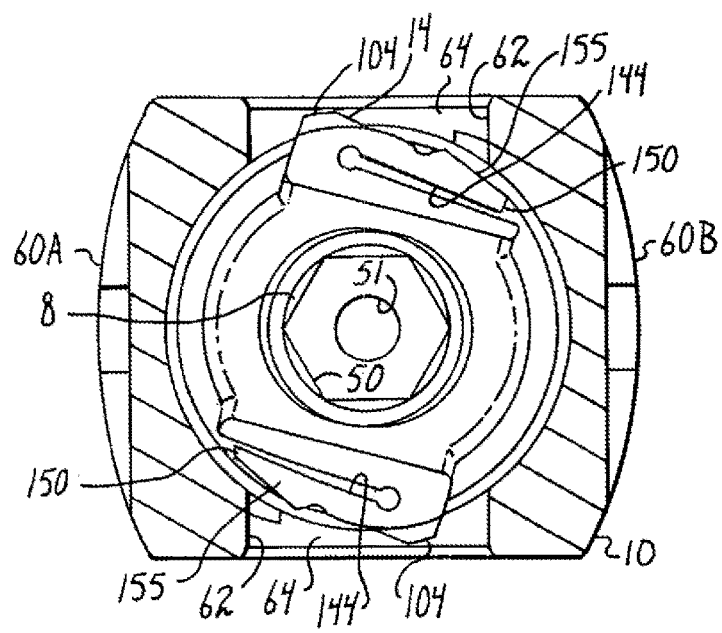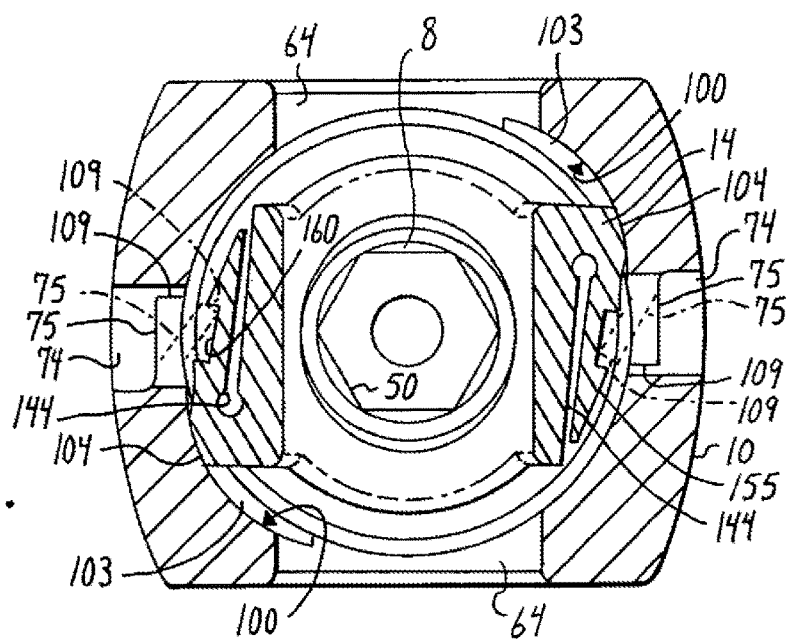

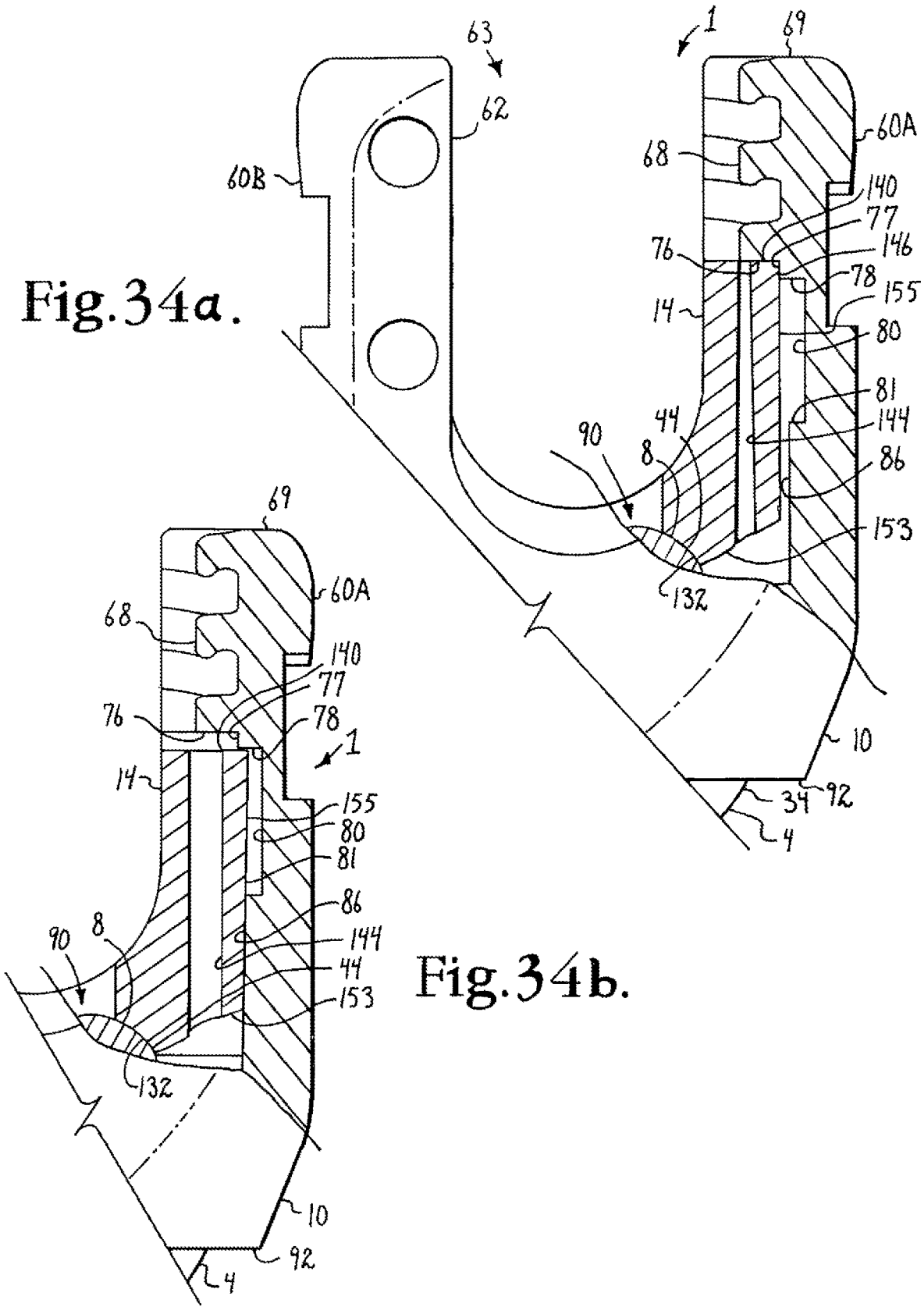

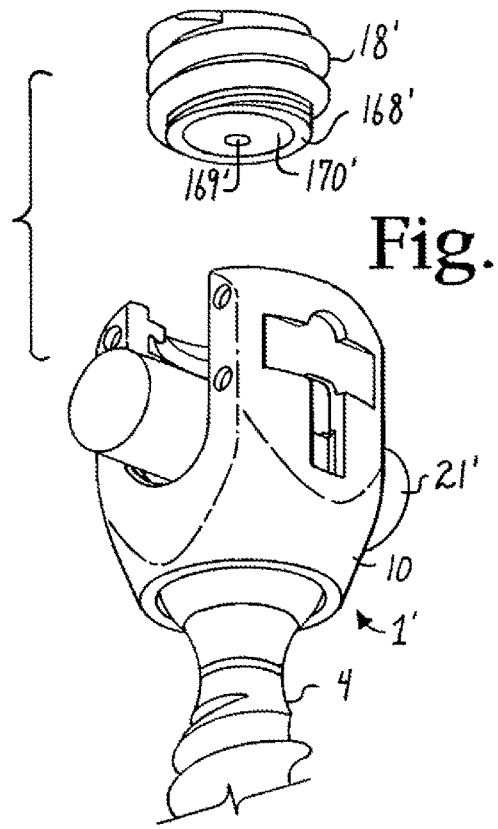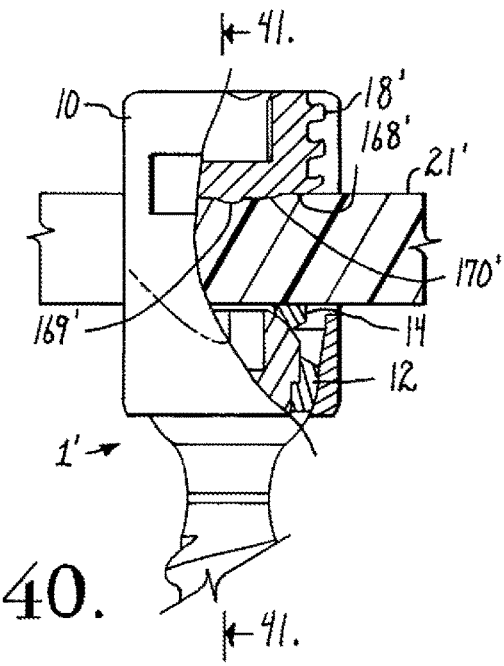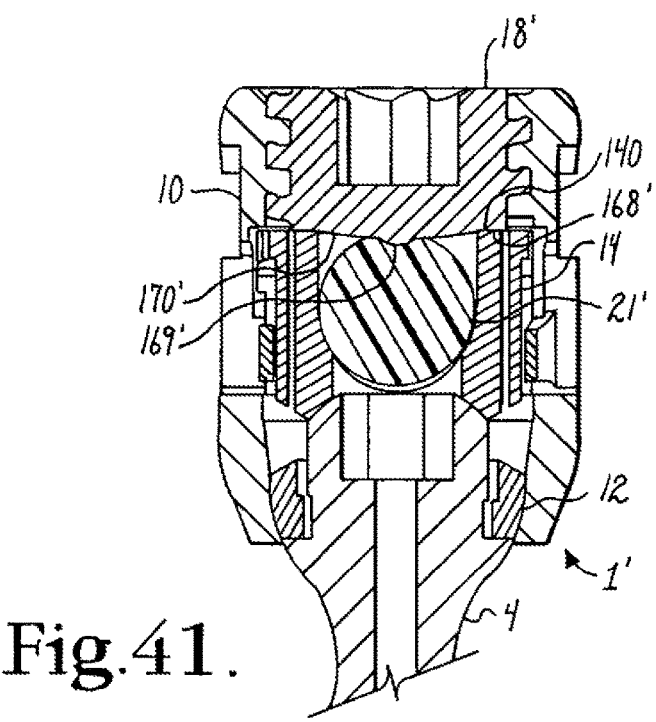
Fig.39.
Fig.40.
Fig.41.

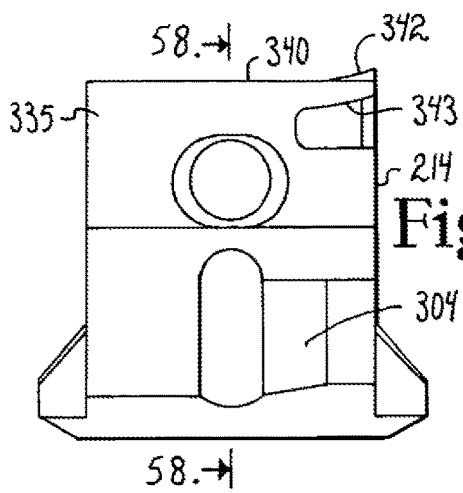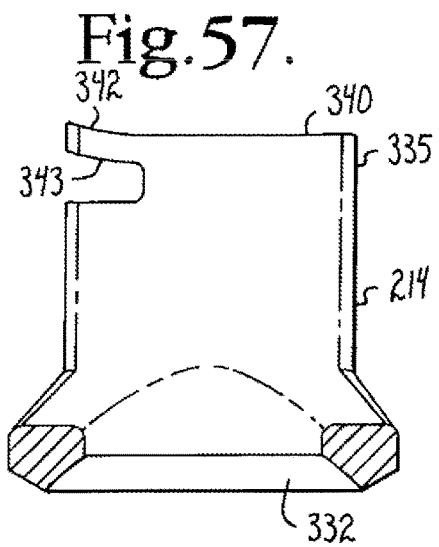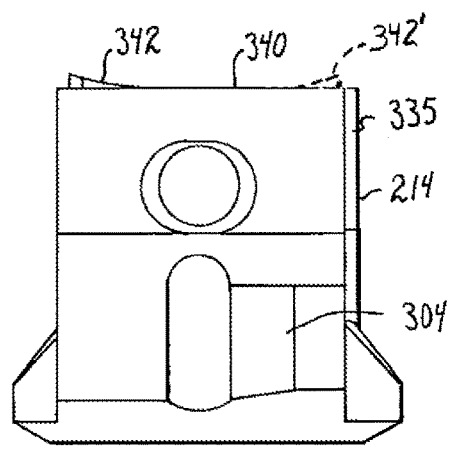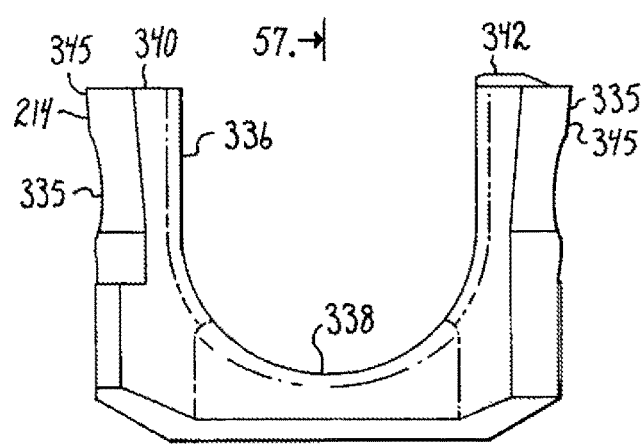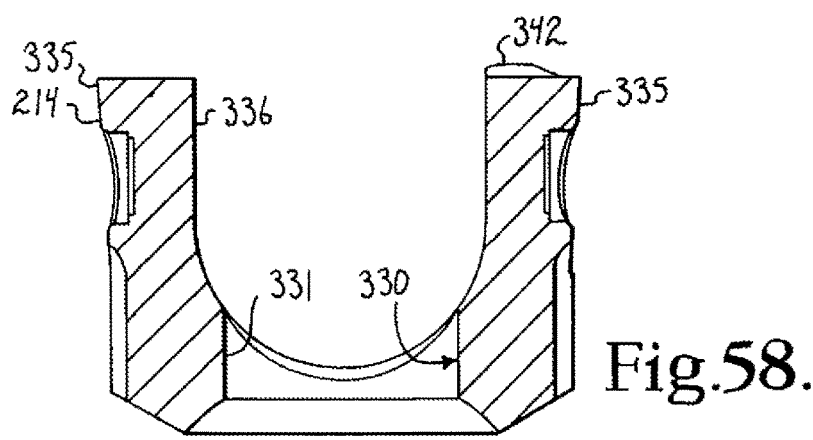

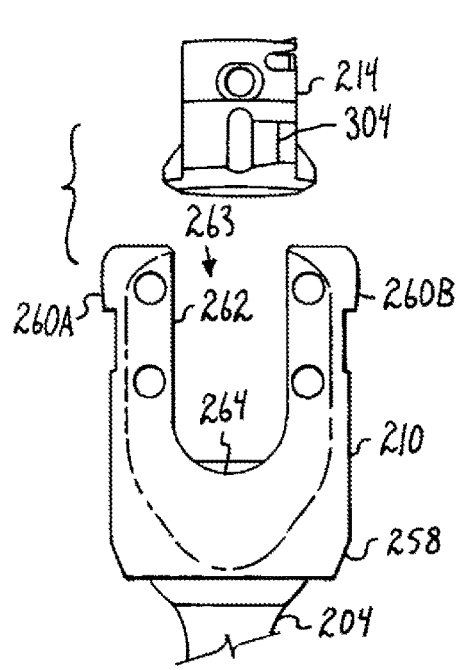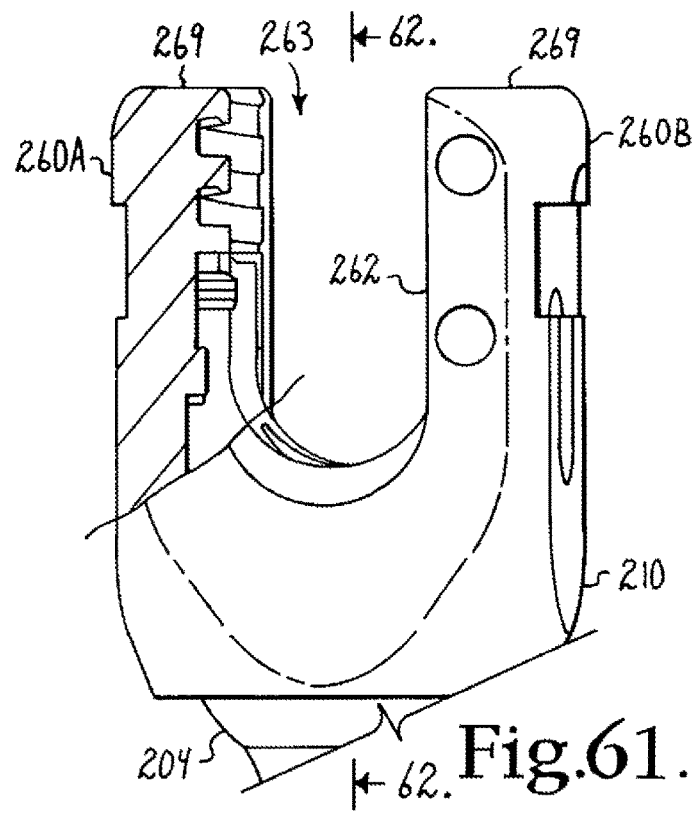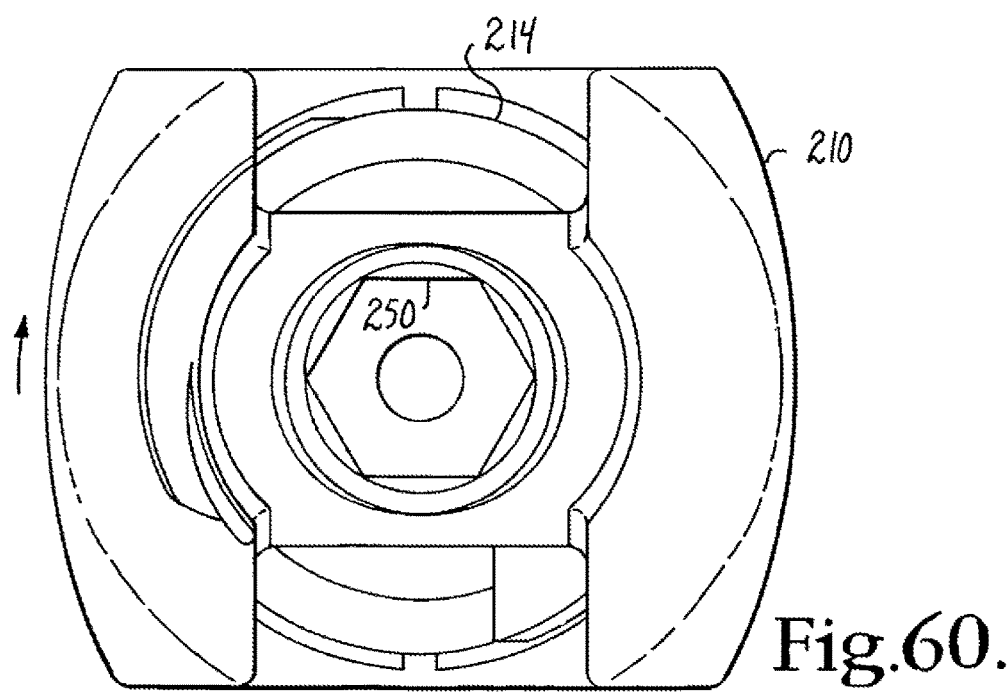
Fig.59.
Fig.61.
Fig.60.

PIVOTAL BONE ANCHOR ASSEMBLY WITH RESILIENTLY BIASED FRICTION FIT INSERT

CROSS-REFERENCE TO RELATED APPLICATIONS

This application is a continuation of U.S. application Ser. No. 17/033,417, filed Sep. 25, 2020, which is a continuation of U.S. application Ser. No. 13/068,506, filed May 12, 2011, now U.S. Pat. No. 10,792,074, which claims the benefit of U.S. Provisional Application No. 61/395,692, filed May 14, 2010, each of which is incorporated by reference in its entirety herein and for all purposes.

BACKGROUND OF THE INVENTION

The present invention is directed to polyaxial bone screws for use in bone surgery, particularly spinal surgery and particularly to such screws with compression or pressure inserts.

Bone screws are utilized in many types of spinal surgery in order to secure various implants to vertebrae along the spinal column for the purpose of stabilizing and/or adjusting spinal alignment. Although both closed-ended and open-ended bone screws are known, open-ended screws are particularly well suited for connections to rods and connector arms, because such rods or arms do not need to be passed through a closed bore, but rather can be laid or urged into an open channel within a receiver or head of such a screw.

Typical open-ended bone screws include a threaded shank with a pair of parallel projecting branches or arms which form a yoke with a U-shaped slot or channel to receive a rod. Hooks and other types of connectors, as are used in spinal fixation techniques, may also include open ends for receiving rods or portions of other structure.

A common mechanism for providing vertebral support is to implant bone screws into certain bones which then in turn support a longitudinal structure such as a rod, or are supported by such a rod. Bone screws of this type may have a fixed head or receiver relative to a shank thereof. In the fixed bone screws, the rod receiver head cannot be moved relative to the shank and the rod must be favorably positioned in order for it to be placed within the receiver head. This is sometimes very difficult or impossible to do. Therefore, polyaxial bone screws are commonly preferred.

Open-ended polyaxial bone screws allow rotation of the head or receiver about the shank until a desired rotational position of the head is achieved relative to the shank. Thereafter, a rod or other longitudinal connecting member can be inserted into the head or receiver and eventually the receiver is locked or fixed in a particular position relative to the shank. During the rod implantation process it is desirable to utilize bone screws or other bone anchors that have components that remain within the bone screw and further remain properly aligned during what is sometimes a very lengthy, difficult procedure.

SUMMARY OF THE INVENTION

A bone anchor assembly according to the invention includes a shank having an upper portion or head and a body for fixation to a bone; a receiver defining an upper open channel, a cavity and a lower opening; a compression insert; and a retainer for capturing the shank upper portion in the receiver, the retainer being in press fit engagement with the shank upper portion, the upper portion and attached retainer being pivotable with respect to the receiver prior to locking of the shank into a desired configuration. The press-fit engagement between the shank upper portion and the retainer may also be described as a cam capture, with the retainer and/or shank upper Portion having a sloping or inclined surface. The shank and retainer cooperate in such a manner that a partial rotation between the retainer and the shank brings the shank and retainer structures into locking engagement. The illustrated compression insert operatively engages the shank upper portion and is spaced from the retainer. The compression insert frictionally engages the shank during assembly, providing non-floppy positioning of the shank with respect to the receiver and also subsequent independent locking of the shank with respect to the receiver. The non-floppy temporary frictional holding is provided by at least one resilient surface on the insert, compression of the resilient surface toward the insert during the temporary frictional holding is by an inner surface of the receiver. When the insert is pressed downwardly into locking engagement with the shank upper portion or head, the resilient surface returns to a neutral or near neutral position, resiliently pressing out against the receiver and locking the insert against the receiver. Thereafter, further manipulation of a rod or other longitudinal connecting member is possible with the otherwise locked screw.

Objects of the invention include providing apparatus and methods that are easy to use and especially adapted for the intended use thereof and wherein the tools are comparatively inexpensive to produce. Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 4 is an enlarged and partial cross-sectional view taken along the line 4-4 of FIG. 2.

FIG. 5 is an enlarged and partial cross-sectional view taken along the line 5-5 of FIG. 2.

FIG. 6 is an enlarged top plan view of the receiver of FIG. 1.

FIG. 7 is an enlarged bottom plan view of the receiver of FIG. 1.

FIG. 8 an enlarged side elevational view of the receiver of FIG. 1.

FIG. 9 is an enlarged front elevational view of the receiver of FIG. 1.

FIG. 10 is an enlarged perspective view of the receiver of FIG. 1.

FIG. 14 is an enlarged perspective view of the retainer of FIG. 1.

FIG. 15 is an enlarged top plan view of the retainer of FIG. 1.

FIG. 16 is an enlarged bottom plan view of the retainer of FIG. 1.

FIG. 17 is an enlarged cross-sectional view taken along the line 17-17 of FIG. 15.

FIG. 18 is an enlarged and partial front elevational view of the shank and retainer of FIG. 1 with show the detail thereof.

FIG. 27 is an enlarged and partial front elevational view of the receiver, retainer and shank of FIG. 1 shown in a stage of assembly subsequent to that shown in FIG. 26, with portions broken away to show the detail thereof and further showing cooperating portions of the shank and retainer in phantom.

FIG. 28 is an enlarged and partial front elevational view of the receiver, retainer and shank of FIG. 1 shown in a stage of assembly subsequent to that shown in FIG. 27, with portions broken away to show the detail thereof and further showing cooperating portions of the shank and retainer in phantom.

FIG. 29 is a reduced front elevational view of the assembled receiver, retainer and shank of FIG. 28, showing a stage of assembly with the insert of FIG. 1, shown in a side elevational loading position.

FIG. 30 is an enlarged cross-sectional view of the receiver, retainer and shank taken along the line 30-30 of FIG. 29 and further showing the insert of FIG. 29 in top plan view, being shown in a stage of assembly within the receiver.

FIG. 31 is an enlarged cross-sectional view of the receiver, retainer and shank taken along the line 31-31 of FIG. 29 and further showing the insert of FIG. 29 in cross-section in a first factory assembled position within the receiver, and also showing in phantom the pair of receiver spring tabs being biased toward the insert.

FIG. 34a is an enlarged and partial rear elevational view of the assembly of FIG. 32 with portions broken away to show the detail thereof, the insert being shown in the factory assembled position.

FIG. 34b is an enlarged and partial rear elevational view of the assembly of FIG. 33 with portions broken away to show the detail thereof, the insert being shown in a subsequent second or locked position with respect to the receiver.

FIG. 39 is an enlarged and partial, partially exploded perspective view of the assembled receiver, shank, retainer and insert of FIGS. 32-34 further shown with an alternative deformable rod and an alternative closure top.

FIG. 40 is a partial side elevational view of the assembly of FIG. 39, shown fully assembled and with portions broken away to show the detail thereof.

FIG. 41 is an enlarged and partial cross-sectional view taken along the line 41-41 of FIG. 40.

FIG. 54 is an enlarged side elevational view of the insert of FIG. 47.

FIG. 55 is an enlarged side elevational view of the insert of FIG. 47 opposite to that shown in FIG. 54.

FIG. 56 is an enlarged front elevational view of the insert of FIG. 47.

FIG. 57 is a cross-sectional view taken along the line 57-57 of FIG. 56.

FIG. 58 is a cross-sectional view taken along the line 58-58 of FIG. 54.

FIG. 59 is an enlarged and partial front elevational view of the assembled receiver, retainer and shank of FIG. 47, shown in exploded view with the insert of FIG. 47, the insert being in a side elevational loading position.

FIG. 60 is an enlarged top plan view of the assembled receiver, retainer and shank of FIG. 47, further showing the insert of FIG. 47 in top plan view, being shown in a stage of assembly within the receiver.

FIG. 61 is an enlarged and partial perspective. view of the assembled receiver, retainer, shank and insert of FIG. 47 with a portion of the receiver broken away to show the detail thereof.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of the bone attachment structures in actual use.

Figure 1:
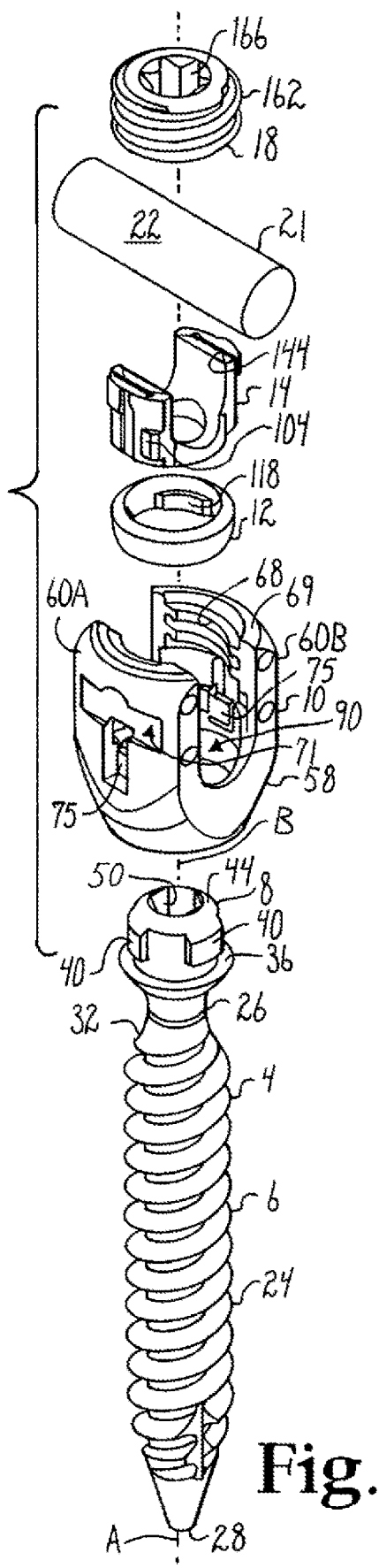
FIG. 1 is an exploded perspective view of a polyaxial bone screw assembly according to the present invention including a shank, a receiver, a retainer and a compression insert and also shown with a closure top and a longitudinal connecting member in the form of a rod.
Figure 2:
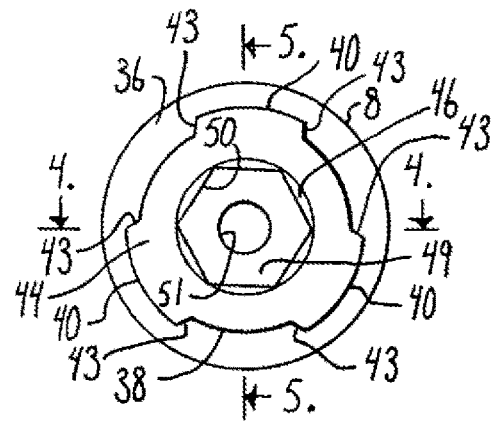
FIG. 2 is an enlarged top plan view of the shank of FIG. 1.
Figure 3:
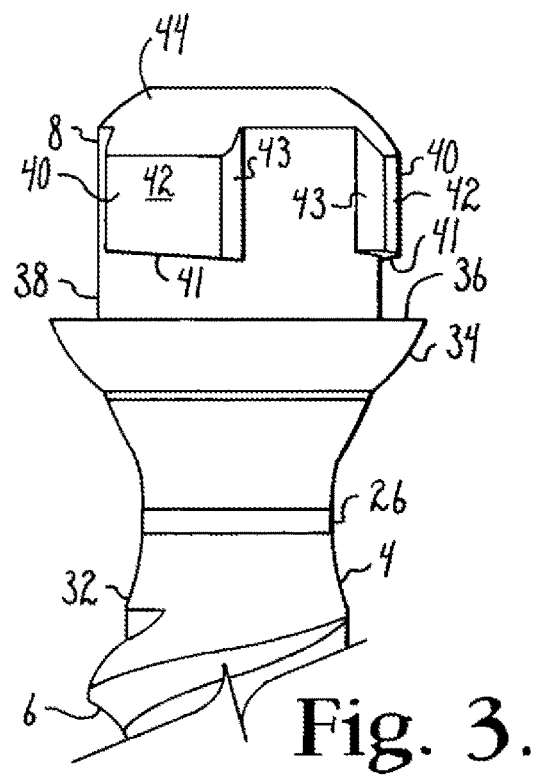
FIG. 3 is an enlarged and partial front elevational view of the shank of FIG. 1.

With reference to FIGS. 1-38 the reference number 1 generally represents a polyaxial bone screw apparatus or assembly according to the present invention. The assembly 1 includes a shank 4, that further includes a body 6 integral with an upwardly extending upper portion or capture structure 8; a receiver 10; a retainer structure 12 and a compression or pressure insert 14. The shank 4, receiver 10, retainer 12 and compression insert 14 are typically factory assembled prior to implantation of the shank body 6 into a vertebra 13, as will be described in greater detail below. FIG. 1 further shows a closure structure 18 of the invention for capturing a longitudinal member, for example, a rod 21 which in turn engages the compression insert 14 chat presses against the shank upper portion 8 into fixed frictional contact with the retainer 12, so as to capture, and fix the longitudinal connecting member 21 within the receiver 10 and thus fix the member 21 relative to the vertebra 13. The illustrated rod 21 is hard, stiff, nonelastic and cylindrical, having an outer cylindrical surface 22. It is foreseen (and also will be described with respect to other embodiments) that the rod 21 may be of a different stiffness, elastic, deformable and/or of a different cross-sectional geometry. The receiver 10 and the shank 4 cooperate in such a manner that the receiver 10 and the shank 4 can be secured at any of a plurality of angles, articulations or rotational alignments relative to one another and within a selected range of angles both from side to side and from front to rear, to enable flexible or articulated engagement of the receiver 10 with the shank 4 until both are locked or fixed relative to each other near the end of an implantation procedure. The assembly is advantageously configured and factory assembled to provide a surgeon with a bone anchor exhibiting sufficient frictional engagement between the compression insert and the shank upper portion that the shank is positionable to a desired angle with respect to the receiver during and after implantation if the shank and prior to locking of the polyaxial mechanism with the closure structure. In other words, the factory supplied assembly includes a shank that is not floppy or loose with respect to the receiver, allowing greater ease in handling and manipulation during the surgical process. Locking of the insert onto the shank upper portion may also be performed prior to locking with the closure top. Furthermore, inserts according to the invention are advantageously configured to allow for a squeeze release to easily provide for repositioning of the angle of the bone screw shank, as will be described in greater detail below.

The shank 4, best illustrated in FIGS. 1-5, is elongate, with the shank body 6 having a helically wound bone implantable thread 24 (single or dual lead thread form) extending from near a neck 26 located adjacent to the upper portion or capture structure 8, to a tip 28 of the body 6 and extending radially outwardly therefrom. During use, the body 6 utilizing the thread 24 for gripping and advancement is implanted into the vertebra 13 leading with the tip 28 and driven down into the vertebra with an installation or driving tool (not shown), so as to be implanted in the vertebra to near the neck 26, as more fully described in the paragraphs below. The shank 4 has an elongate axis of rotation generally identified by the reference letter A.

The neck 26 extends axially upward from the shank body 6. The neck 26 may be of the same or is typically of a slightly reduced radius as compared to an adjacent upper end or top 32 of the body 6 where the thread 24 terminates. Further extending axially and outwardly from the neck 26 is the shank upper portion 8 that provides a connective or capture apparatus disposed at a distance from the upper end 32 and thus at a distance from the vertebra 13 when the body 6 is implanted in such vertebra.

The shank upper portion 8 is configured for a pivotable connection between the shank 4 (with attached retainer 12) and the receiver 10 prior to fixing of the shank 4 in a desired position with respect to the receiver 10. The shank upper portion 8 has an outer, convex and substantially spherical lower surface 34 that extends outwardly and upwardly from the neck 26 and terminates at a substantially planar ledge or shelf 36 that is annular and disposed perpendicular to the shank axis A. The shelf 36 is sized and shaped to receive and seat the retainer 12 at a bottom surface thereof as will be described in greater detail below. The spherical lower surface 34 has an outer radius that is the same or substantially similar to an outer radius of the retainer 12 as will be described in greater detail below, the surface 34 as well as the retainer 12 outer surface participating in the ball and socket joint formed by the shank 4 and attached retainer 12 within the partially spherical surface defining an inner cavity of the receiver 10. Extending upwardly from the ledge 36 is a cylindrical surface 38, the surface 38 having a radius that is smaller than the radius of the lower spherical surface 34. Extending substantially radially outwardly from the cylindrical surface 38 are three evenly spaced cam projections or lugs 40, each with a lower surface or ledge 41 that faces toward the ledge 36 and is disposed at a slight angle with respect thereto. As will be discussed in greater detail below, the lower ledge 36, cylindrical surface 38 and upper ledges 41 cooperate to capture and fix the retainer 12 to the shank upper portion 8, prohibiting movement of the retainer 12 along the axis A once the retainer 12 is located between the ledges 36 and 41. It is noted that according to the invention, one, two, three or more cam projections 40 may be disposed about the cylindrical surface 38. Each of the projections 40 further include an outer substantially cylindrical surface 42 bounded by opposed side surfaces 43. A partially spherical or domed top surface 44 partially defines each of the projections 40, terminating at the projection surfaces 42 and the cylindrical surface 38 located between each of the cam projections 40. The spherical surface 44 has an outer radius configured for sliding cooperation and ultimate frictional mating with a substantially spherical concave surface of the compression insert 14 that has the same or substantially similar radius as the surface 44. The radius of the surface 44 is smaller than the radius of the lower spherical surface 34. Located near or adjacent to the surface 44 is an annular top surface 46. A counter sunk substantially planar base or seating surface 49 partially defines an internal drive feature or imprint 50. The illustrated internal drive feature 50 is an aperture formed in the top surface 46 and has a hex shape designed to receive a hex tool (not shown) of an Allen wrench type, into the aperture for rotating and driving the bone screw shank 4. It is foreseen that such an internal tool engagement structure may take a variety of tool-engaging forms and may include one or more apertures of various shapes, such as a pair of spaced apart apertures or a multi-lobular or star-shaped aperture, such as those sold under the trademark TORX, or the like. The seat or base 49 of the drive feature 50 is disposed perpendicular to the axis A with the drive feature 49 otherwise being coaxial with the axis A. In operation, a driving tool is received in the internal drive feature 50, being seated at the base 49 and engaging the six faces of the drive feature 50 for both driving and rotating the shank body 6 into the vertebra 13, either before the shank 4 is attached to the receiver 10 or after the shank 4 is attached to the receiver 10, with the shank body 6 being driven into the vertebra 13 with the driving tool extending into the receiver 10.

The shank 4 shown in the drawings is cannulated, having a small central bore 51 extending an entire length of the shank 4 along the axis A. The bore 50 is defined by an inner cylindrical wall of the shank 4 and has a circular opening at the shank tip 28 and an upper opening communicating with the internal drive 50 at the surface 49. The bore 51 is coaxial with the threaded body 6 and the upper portion 8. The bore 51 provides a passage through the shank 4 interior for a length of wire (not shown) inserted into the vertebra 13 prior to the insertion of the shank body 6, the wire providing a guide for insertion of the shank body 6 into the vertebra 13.

To provide a biologically active interface with the bone, the threaded shank body 6 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate $(Ca_3(PO_4)_2$, tetra-calcium phosphate $(Ca_4P_2O_9)$, amorphous calcium phosphate and hydroxyapatite (Cam) $(PO_4)_6$ $(OH)_2)$. Coating with hydroxyapatite, for example, is desirable as hydroxyapatite is chemically similar to bone with respect to mineral content and has been identified as being bioactive and thus not only supportive of bone ingrowth, but actively taking part in bone bonding.

With particular reference to FIGS. 1 and 6-13, the receiver 10 has a generally U-shaped appearance with a partially discontinuous substantially cylindrical inner and outer profiles. The receiver 10 has an axis of rotation B that is shown in FIG. 1 as being aligned with and the same as the axis of rotation A of the shank 4, such orientation being desirable, but not required during assembly of the receiver 10 with the shank 4. After the receiver 10 is pivotally attached to the shank 4, either before or after the shank 4 is implanted in a vertebra 13, the axis B is typically disposed at an angle with respect to the axis A, as shown, for example, in FIG. 33.

The receiver 10 includes a partially cylindrical and partially frusto-conical base 58 integral with a pair of opposed upstanding arms 60A and 60B, the arms forming a cradle and defining a U-shaped channel 62 between the arms 60A and B with an upper opening, generally 63, and a U-shaped lower seat 64, the channel 62 having a width for operably snugly receiving the rod 21 between the arms 60A and B. Each of the arms 60A and 60B has an interior surface, generally 66, that has a cylindrical profile and further includes a partial helically wound guide and advancement structure 68 extending radially inwardly from the surface 66 and located adjacent top surfaces 69 of each of the arms 60. In the illustrated embodiment, the guide and advancement structure 68 is a partial helically wound interlocking flange-form configured to mate under rotation with a similar structure on the closure structure 18, as described more fully below. However, it is foreseen that the guide and advancement structure 68 could alternatively be a square-shaped thread, a buttress thread, a reverse angle thread or other thread-like or non-thread-like helically wound discontinuous advancement structure for operably guiding under rotation and advancing the closure structure 18 downward between the arms 60, as well as eventual torquing when the closure structure 18 abuts against the rod 21.

An opposed pair of tool receiving and engaging features, generally 71, are formed on outer surfaces 72 of the arms 60A and 60B. The illustrated features 71 are in a T-shape form and include and upper groove or recess 73 running substantially parallel to the respective top surface 69 that does not extend through the respective arm 60A or 60B and a connecting transverse, substantially rectangular lower recess or through bore 74 that does extend from each arm outer surface 72 to each interior surface 66, providing access to laterally extending spring tabs 75 that bias against the pressure insert 14 to prohibit reverse (illustrated as counter-clockwise) rotational movement of the insert about the receiver axis once the insert is loaded in the receiver 10, as will be described in greater detail below. The aperture feature 71 and alternatively, any additional tool receiving and engaging apertures may be formed in the receiver outer surfaces and used for holding the receiver 10 during assembly with the shank 4, the retainer 12 and the insert 14, during the implantation of the shank body 6 into a vertebra when the shank is pre-assembled with the receiver 10, and during assembly of the bone anchor assembly 1 with the rod 21 and the closure structure 18. It is foreseen that tool receiving grooves or apertures may be configured in a variety of shapes and sizes and be disposed at other locations on the receiver arms 60A and 60B.

Figure 11:
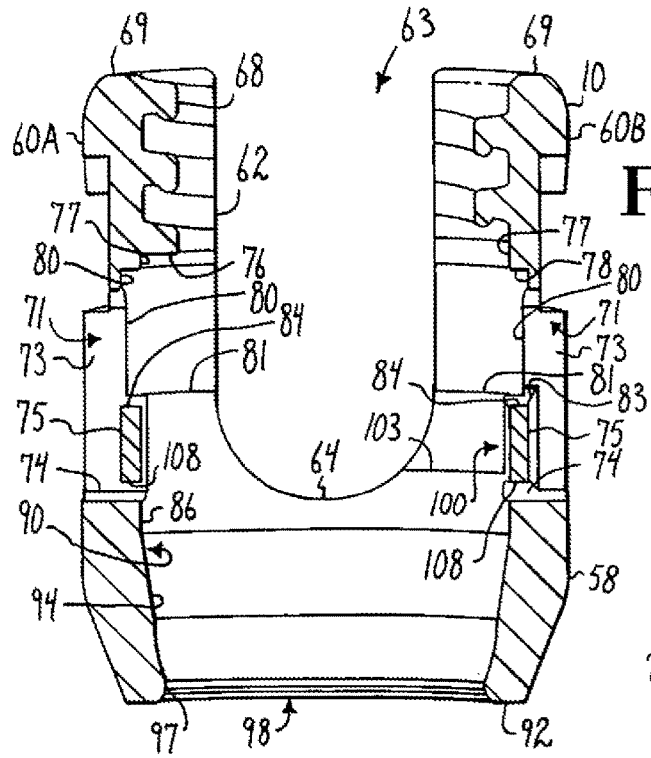
FIG. 11 is an enlarged cross-sectional view taken along the line 11-11 of FIG. 8.

Returning to the interior surface 66 of the receiver arms 60A and 60B, located below the guide and advancement structure 68 on each of the arms is a discontinuous cylindrical surface 77, having a diameter approximately the same as a greater diameter of the guide and advancement structure 68. The space under the guide and advancement structure 68 that is defined in part by the cylindrical surface 77 forms a run-out area for the closure top 18. With particular reference to FIG. 11, on the arm 60A, the cylindrical surface 77 is adjacent to an upper surface or ledge 76 that partially defines the flange form 68 run-out and also serves as an intermediate or temporary abutment feature (along with the cylindrical surface 77) for the insert 14 as shown, for example, in FIG. 34a, and as will be discussed in greater detail below. Adjacent to and located below the cylindrical surface 77 is a discontinuous annular surface 78 that in turn is adjacent to a discontinuous substantially cylindrical surface 80. The surface 80 extends from the surface 78 to an annular lip or ledge 81 that is disposed perpendicular to the axis B and extends radially inwardly toward the axis B. On each arm 60A and 60B, a portion of the ledge 81 is adjacent to and integral with a sloping or curved transition surface 83 that in turn is adjacent to and integral with an upper surface 84 of the respective spring tab 75. Adjacent to the annular lip 81 is another partially discontinuous substantially cylindrical surface 86 that partially defines the arms 60A and 60B as well as extends into the base 58. Thus the surface 86 also partially defines the lower seat 64 of the U-shaped channel 62. An inner surface 88 of the spring tab 75 is integral with the surface 86. The surface 86 has a diameter smaller than the diameter of the cylindrical surface 80, but larger than the diameter of the surface 77; this diameter feature will come into play with respect to the cooperation between the insert 14 and the receiver inner surfaces 76, 77, 78 and 86 as will be described in detail below. As mentioned above, the surface 86 also partially defines an inner cavity, generally 90, of the base 58 of the receiver 10, the cavity 90 and the U-shaped channel 62 defining a through bore of the receiver 10 from the top surface 69 to a bottom surface 92 thereof. Moving downwardly further into the base cavity 90, a substantially conical surface 94 is adjacent to the cylindrical surface 86 and terminates at a radiused or spherical seating surface 96. It is noted that the surface 94 as well as portions of the surface 86 may be partially spherical or otherwise curved in some embodiments of the invention. The surface 96 is sized and shaped for slidably mating with the retainer structure 12 and ultimately frictionally mating therewith as will be described in greater detail below. The spherical seating surface 96 is adjacent a flared surface or as shown, a series of beveled surfaces that provide a neck 97 that forms a bottom opening, generally 98, to the cavity 90 at the receiver bottom surface 92. The neck 97 is sized and shaped to be smaller than an outer radial dimension of the retainer 12 when the retainer 12 is fixed to the shank upper portion 8, so as to form a restriction to prevent the structure 12 and attached shank portion 8 from passing through the cavity 90 and out the lower exterior 92 of the receiver 10 during operation thereof.

Figure 12:
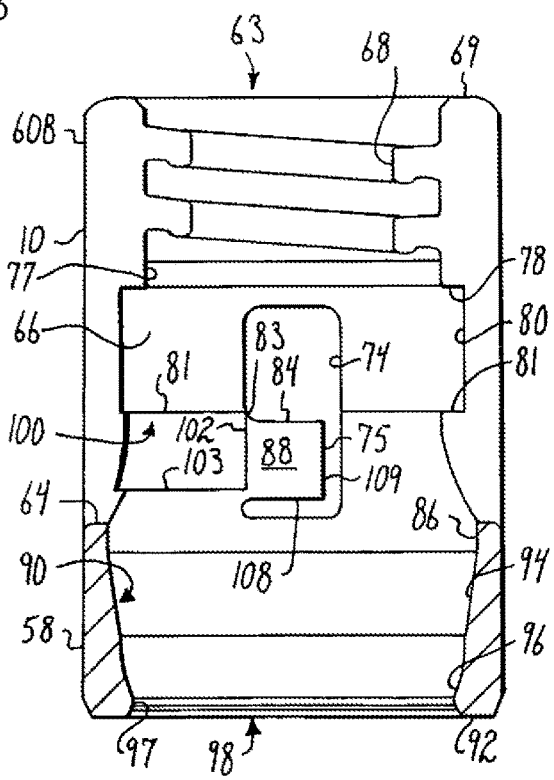
FIG. 12 is an enlarged cross-sectional view taken along the line 12-12 of FIG. 9.
Figure 13:
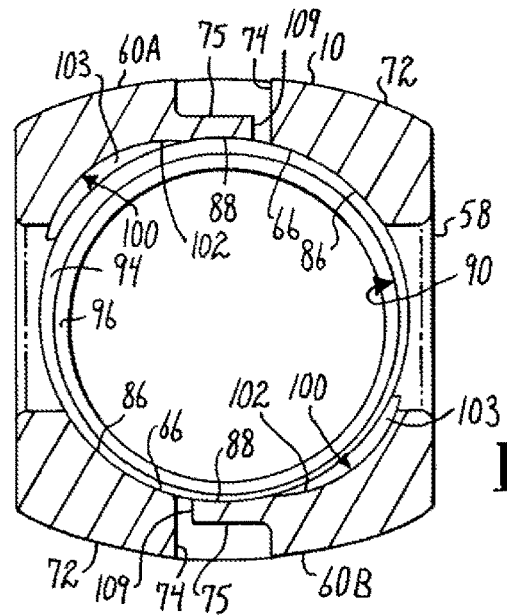
FIG. 13 is an enlarged cross-sectional view taken along the line 13-13 of FIG. 8.
Figure 19:
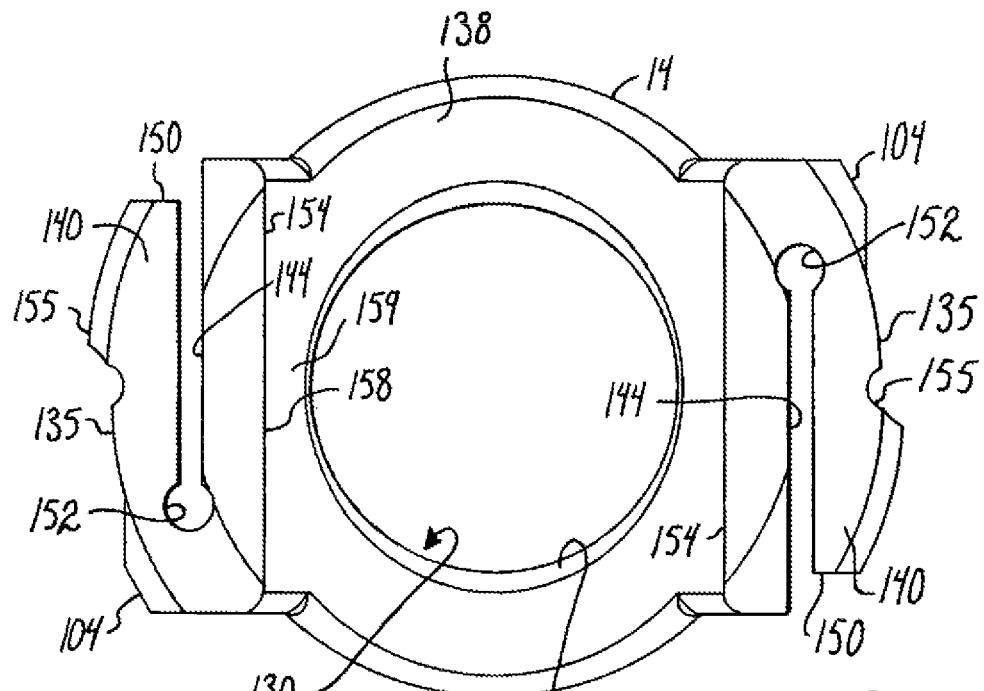
FIG. 19 is an enlarged top plan view of the insert of FIG. 1.
Figure 20:
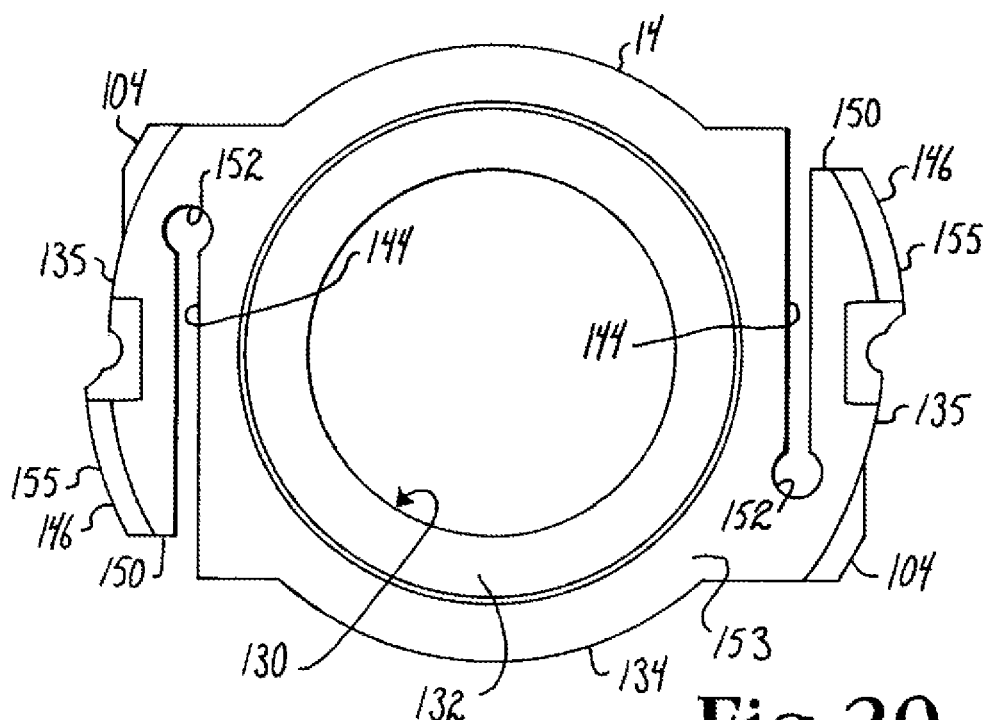
FIG. 20 is an enlarged top plan view of the insert of FIG. 1.
Figure 21:
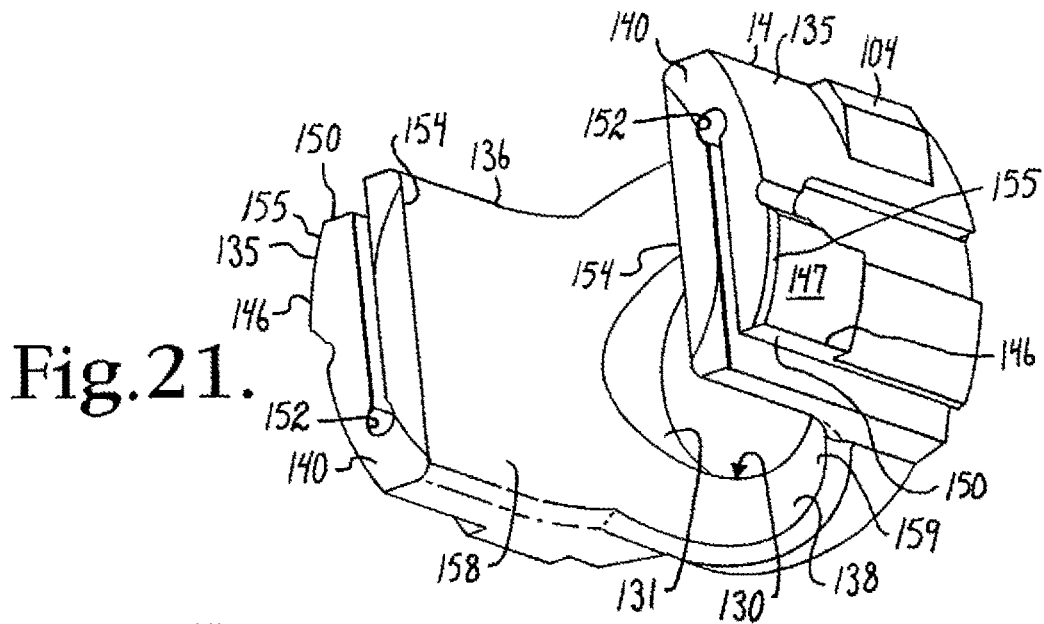
FIG. 21 is an enlarged top plan view of the insert of FIG. 1.
Figure 22:
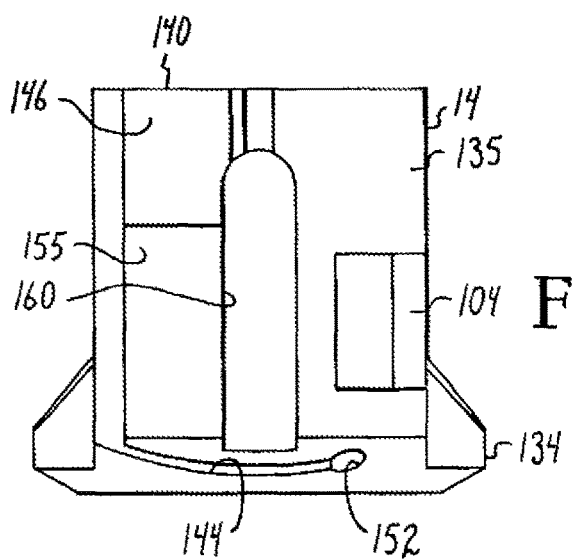
FIG. 22 is an enlarged top plan view of the insert of FIG. 1.
Figure 23:
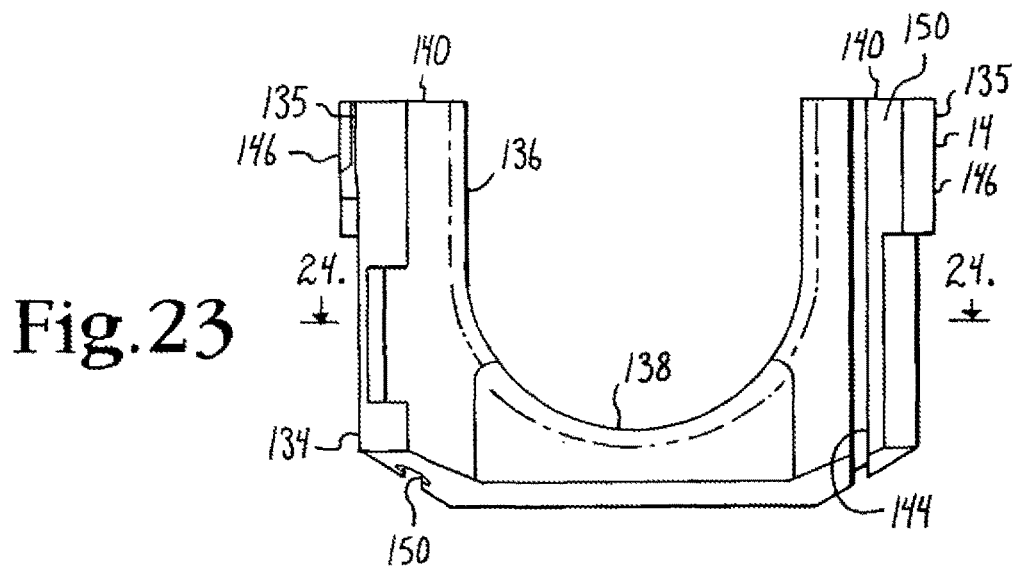
FIG. 23 is an enlarged front elevational view of the insert of FIG. 1
Figure 24:
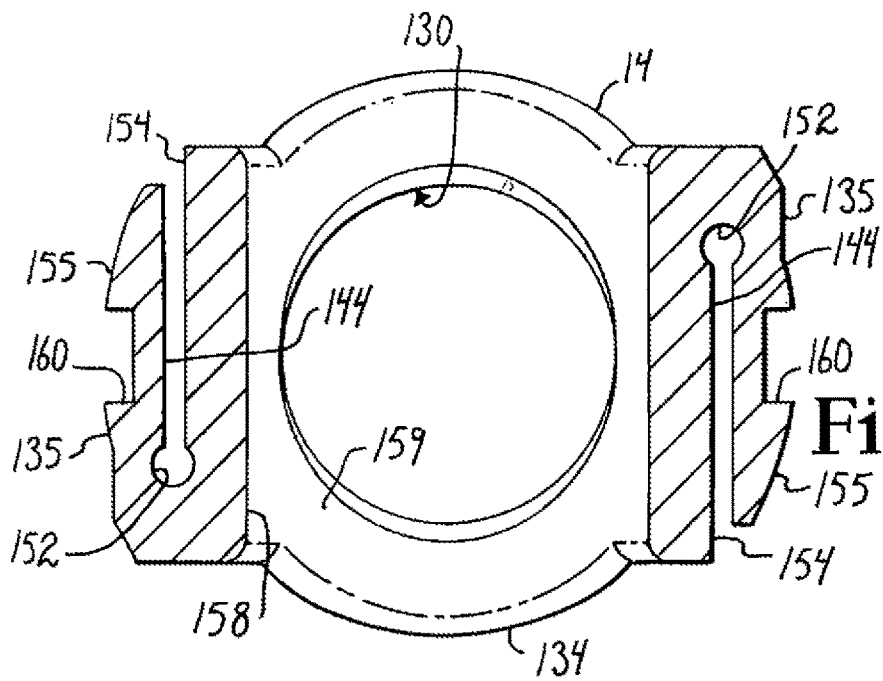
FIG. 24 is an enlarged cross-sectional view taken along the line 24-24 of FIG. 23.

Returning to the surface 86, with reference to FIGS. 12 and 13, and in particular to the surface 86 that extends upwardly into the arms 60A and 60B, formed within each of the substantially cylindrical surfaces 86 and located directly beneath the annular lip 81 is a recess, generally 100, partially defined by a rounded stop or abutment wall 102 and partially defined by a lower annular lip or ledge 103. As will be described in greater detail below, the cooperating compression insert 14 includes a cooperating structure 104 that extends outwardly from each arm thereof that abuts against the respective abutment wall 102 of each of the receiver arms, providing a centering stop or block when the insert 14 is rotated into place in a clockwise manner as will be described below.

Finally, returning to the laterally extending spring tabs 75, that include top surfaces 84 and inner surfaces 68 previously described herein, each spring tab 75 further includes a bottom surface 108 and an end surface 109. The surface 109 is adjacent to and extends between the surfaces 108 and 84, the end surface 109 running substantially parallel to the receiver axis B. The end surfaces 109 of the opposing spring tabs 75 generally face in opposite directions. As described more fully below and shown, for example, in FIG. 31, during assembly, the tabs 75 'are pressed radially inwardly to engage the insert 14 and prohibit counter-clockwise motion of the insert 14 with respect to the receiver 10.

With particular reference to FIGS. 1 and 14-18, the retainer 12 that operates to capture the shank upper portion 8 within the receiver 10 has a central axis that is operationally the same as the axis A associated with the shank 4 when the shank upper portion 8 and the retainer 12 are installed within the receiver 10. The retainer 12 is typically made from a hard material, that also may be resilient, such as stainless steel or titanium alloy, for embodiments (not shown) having a slit or slot that would allow for top or bottom loading, so that the retainer 12 may be contracted or expanded during assembly. The retainer structure 12 has a central bore, generally 110, that passes entirely through the retainer structure 12 from a top surface 112 to a bottom surface 114 thereof. The bottom surface 114 is substantially planar and disposed perpendicular to the axis A when the retainer is fixed to the shank 4 with the surface 114 abutting the shank surface 36 as shown, for example, in FIG. 18. The top surface 112 is disposed at an angle with respect to the axis A when the retainer 12 is fixed to the shank 4, the surface 112 sloping radially downwardly to provide space and clearance between the retainer 12 and the insert 14 when the assembly 1 is fully assembled and placed at any angle of inclination of the shank 4 with respect to the receiver 10. A first inner cylindrical surface 116 defines a substantial portion of the bore 110. The cylindrical surface 116 is sized and shaped to be slidingly received about the cylindrical surface portion 38 of the shank upper portion 8. Extending inwardly radially from the surface 116 are three evenly spaced cam projections or shelves 118 sized and shaped to cooperate with the cam projections 40 of the shank upper portion 8 for fixing the retainer 12 to the shank upper portion 8. The cam shelves 118 extend from at or near the retainer bottom 114 to a location spaced from the retainer top 112. The cam shelves 118 are sized and shaped to provide direct mating support with each shank projection 40. The cam shelves 118 are also spaced from the top surface 112 to provide adequate space for loading rotation and placement of the cam projections 40 of the shank upper portion 8 with respect to the retainer 12 during assembly within the receiver 10 of the bone screw 1. Each of the illustrated cam shelves 118 includes an upper, sloping or slanted seating surface 120 and an opposed bottom surface 122 that is flush and integral with the bottom surface 114 of the retainer 12. The illustrated camming seating surfaces 120 are each disposed about midway between the top 112 and the bottom 114 of the retainer 12, but may be located slightly higher or lower along the surface 116. Each camming shelf 118 further includes opposed side surfaces 124 and 125 running from the bottom surface 114 to the seating surface 120. Each of the surfaces 124 and 125 are curved and substantially concave. Each shelf includes an inner cylindrical surface 126 sized and shaped to slidingly mate with the surfaces 42 of the cam projections 40 of the shank upper portion 8. The sloping seating surfaces 120 are sized to receive the lugs or projections 40 at the surfaces 41 thereof, with the surfaces 36 and 41 of the shank upper portion forming a cam track between which each camming shelf 118 slides and is captured and frictionally fixed. A degree of inclination of the surface 120 substantially matches a degree of inclination of the bottom surface 41 of the lug 40. In the illustrated embodiment, the degree of inclination is about three degrees, but it is foreseen that it may be more or less than that illustrated. In some embodiments according to the invention, one or both the ramped surfaces 41 and 120 include a roughening, ridges or some other treatment to further aid frictional locking of the retainer 12 with respect to each lug 40. Furthermore, in some embodiments of the invention, fixing engagement between the lugs 40 and the shelves 122 may be enhanced by a weld or adhesive. For example, the illustrated camming shelves 118 are slightly wider than the shank projections 40 at the side surfaces 124 and 125 so as to advantageously accommodate a spot weld or other fixing or adhering structure or substance.

The retainer 12 also has a radially outer partially spherically shaped surface 129 sized and shaped to mate with the partial spherical shaped seating surface 96 of the receiver 10. The surface 129 includes an outer radius that is larger than a radius of the lower opening 98 of the receiver 10, thereby prohibiting the retainer 12 and the shank upper portion 8 from passing through the opening 98 once the retainer 12 is fixed to the shank upper portion 8 within the receiver cavity 90. Although not required, it is foreseen that the outer partially spherically shaped surface 129 may be a high friction surface such as a knurled surface or the like.

With particular reference to FIGS. 1 and 19-24, the compression or pressure insert 14 is illustrated that is sized and shaped to be received by and down-loaded into the receiver 10 through the channel opening 66 as illustrated in FIGS. 29-31. The compression insert 14 has an operational central axis that is the same as the central axis B of the receiver 10. The compression insert 14 has a central channel or through bore, generally 130, substantially defined by an inner substantially cylindrical surface 131 coaxial with an inner partially spherical surface 132. The compression insert 14 through bore is sized and shaped to receive a driving tool (not shown) therethrough that engages the shank drive feature 50 when the shank body 6 is driven into bone with the receiver 10 attached. The surface 132 is sized and shaped to slidingly receive and ultimately frictionally engage the substantially spherical or domed surface 44 of the shank upper portion 8 such that the surface 44 initially frictionally slidingly and pivotally mates with the spherical surface 132 to create a ball-and-socket type joint. The surfaces 44 and/or 132 may include a roughening or surface finish to aid in frictional contact between them once a desired angle of articulation of the shank 4 with respect to the receiver 10 is reached.

The compression insert 14 includes a substantially cylindrical base body 134 integral with a pair of upstanding arms 135. The bore 130 is disposed primarily within the base body 134 and communicates with a generally U-shaped through channel 136 that is defined by the upstanding arms 135. The channel 136 has a lower seat 138 sized and shaped to closely, snugly engage the rod 21. It is foreseen that an alternative embodiment may be configured to include planar holding surfaces that closely hold a square or rectangular bar as well as hold a cylindrical rod-shaped or corded longitudinal connecting member. The arms 135 disposed on either side of the channel 136 extend outwardly and upwardly from the body 134, The arms 135 are sized and configured for ultimate placement near the run-out below the receiver guide and advancement structure 68. It is foreseen that in some embodiments of the invention, the arms may be extended and the closure top configured such the arms ultimately directly engage the closure top for locking of the polyaxial mechanism. In the present embodiment, the arms 135 include top surfaces 140 that are ultimately positioned in spaced relation with the closure top 18, so that the closure top 18 frictionally engages and holds the rod 21, pressing the rod 21 downwardly against the seating surface 138, the insert 14 in turn pressing against the domed top 44 of the shank 4 to lock the polyaxial mechanism of the bone screw assembly 1. The illustrated insert 14 further includes features that allow for a non-floppy frictional fit between the insert and the shank 4 during assembly and also for a locking of the insert 14 with respect to the shank 4 prior to locking down of the closure top 18. These features include a key-hole like through slot 144 disposed within each arm 135 running substantially vertically from the top surface 140 and through the base body 134. Furthermore, each arm 135 includes at least one radially projected upper portion 146 with an outer partially cylindrical surface 147 for engaging with the receiver 10 as will be described more fully below. It is foreseen that inserts 14 according to the invention may have at least one and up to a Plurality of such portions 146. The illustrated slots 144 open along opposed side surfaces 150 of the arms, the side surfaces 150 each also defining a portion of one of the projected upper portions 146. Each slot 144 terminates at a cylindrical through bore 152 that also runs from the top surface 140 through the base body 134 and out a base surface 153, the bore 152 being spaced from inner and outer surfaces of each of the arms 135. Each slot 144 separates each arm 135 into an inner arm portion 154 and an outer arm portion 155 that includes the respective projected upper portion 146, the portions 155 being compressible towards the portions 154 during assembly of the insert 14 within the receiver 10 as will be described in greater detail below. Each arm 135 further includes inner planar walls 158 and inner sloping lower surfaces 159. Each outer arm portion 155 further includes a generally vertically extending recess or partial aperture 160 sized and shaped to receive holding tabs 75, or, in some embodiments of the invention, crimped material from the receiver.

The pressure insert body 134 located between the arms 135 has an outer diameter slightly smaller than a diameter between crests of the guide and advancement structure 68 of the receiver 10 allowing for top loading of the compression insert 14 into the receiver opening 63, with the arms 135 of the insert 14 being located between the receiver arms 60A and 60B during insertion of the insert 14 into the receiver 10. Once located between the guide and advancement structure above and the shank upper portion 8 below, the insert 14 is rotated into place about the receiver axis until the arms 135 are directly below the guide and advancement structure 68 as will be described in greater detail below. At some point in the assembly, a tool (not shown) may be inserted into the receiver apertures to press the tabs 75 into the insert recesses 160. It is noted that assembly of the shank 4 with the retainer 12 within the receiver 10, followed by insertion of the lower compression insert 14 into the receiver 10 are assembly steps typically performed at the factory, advantageously providing a surgeon with a polyaxial bone screw with the lower insert 14 already held in alignment with the receiver 10 and providing a non-floppy, but pivotable shank ready for insertion into a vertebra. The compression or pressure insert 14 ultimately seats exclusively on the surface 44 of the shank upper portion 8, with the base surface 153 sloping upwardly and away from the shank upper portion 8, providing clearance between the retainer 12 and the insert 14 during pivoting of the shank 4 with respect to the receiver 10. The assembly may be configured so that the insert 14 extends at least partially into the receiver U-shaped channel 62.

With reference to FIGS. 1 and 35-38, the illustrated elongate rod or longitudinal connecting member 21 can be any of a variety of implants utilized in reconstructive spinal surgery, but is typically a cylindrical, elongate structure having the outer substantially smooth, cylindrical surface 22 of uniform diameter. The rod 21 may be made from a variety of metals, metal alloys and deformable and less compressible plastics, including, but not limited to rods made of elastomeric, polyetheretherketone (PEEK) and other types of materials.

Longitudinal connecting members for use with the assembly 1 may take a variety of shapes, including but not limited to rods or bars of oval, rectangular or other curved or polygonal cross-section. The shape of the insert 14 may be modified so as to closely hold, and if desired, fix or slidingly capture the longitudinal connecting member to the assembly 1. Some embodiments of the assembly 1 may also be used with a tensioned cord. Such a cord may be made from a variety of materials, including polyester or other plastic fibers, strands or threads, such as polyethylene-terephthalate. Furthermore, the longitudinal connector may be a component of a longer overall dynamic stabilization connecting member, with cylindrical or bar-shaped portions sized and shaped for being received by the compression insert 14 of the receiver having a U-shaped channel (or rectangular- or other-shaped channel) for closely receiving the longitudinal connecting member. The longitudinal connecting member may be integral or otherwise fixed to a bendable or damping component that is sized and shaped to be located between adjacent pairs of bone screw assemblies 1, for example. A damping component or bumper may be attached to the longitudinal connecting member at one or both sides of the bone screw assembly 1. A rod or bar (or rod or bar component) of a longitudinal connecting member may be made of a variety of materials ranging from deformable plastics to hard metals, depending upon the desired application. Thus, bars and rods of the invention may be made of materials including, but not limited to metal and metal alloys including but not limited to stainless steel, titanium, titanium alloys and cobalt chrome; or other suitable materials, including plastic polymers such as polyetheretherketone (PEEK), ultra-high-molecular weight-polyethylene (UHMWP), polyurethanes and composites, including composites containing carbon fiber, natural or synthetic elastomers such as polyisoprene (natural rubber), and synthetic polymers, copolymers, and thermoplastic elastomers, for example, polyurethane elastomers such as polycarbonate-urethane elastomers.

With reference to FIGS. 1 and 36-38, the closure structure or closure top 18 shown with the assembly 1 is rotatably received between the spaced arms 60A and 60B. It is noted that the closure 18 can be any of a variety of different types of closure structures for use in conjunction with the present invention with suitable mating structure on the upstanding arms 60A and 60B. It is also foreseen that the closure top could be a twist-in or slide-in closure structure. The illustrated closure structure 18 is substantially cylindrical and includes an outer helically wound guide and advancement structure 162 in the form of a flange form that operably joins with the guide and advancement structure 68 disposed on the arms 60A and 60B of the receiver 10. The flange form utilized in accordance with the present invention may take a variety of forms, including those described in Applicant's U.S. Pat. No. 6,726,689, which is incorporated herein by reference. It is also foreseen that according to the invention the closure structure guide and advancement structure could alternatively be a buttress thread, a square thread, a reverse angle thread or other thread like or non-thread like helically wound advancement structure for operably guiding under rotation and advancing the closure structure 18 downward between the arms 60A and 60B and having such a nature as to resist splaying of the arms when the closure structure 18 is advanced into the U-shaped channel 62. The illustrated closure structure 18 also includes a top surface 164 with an internal drive 166 in the form of an aperture that is illustrated as a star-shaped internal drive such as that sold under the trademark TORX, or may be, for example, a hex drive, or other internal drives such as slotted, tri-wing, spanner, two or more apertures of various shapes, and the like. A driving tool (not shown) sized and shaped for engagement with the internal drive 166 is used' for both rotatable engagement and, if needed, disengagement of the closure 18 from the receiver arms 60A and 60B. It is also foreseen that the closure structure 18 may alternatively include a break-off head designed to allow such a head to break from a base of the closure at a preselected torque, for example, 70 to 140 inch pounds. Such a closure structure would also include a base having an internal drive to be used for closure removal. A base or bottom surface 168 of the closure is planar and further includes a point 169 and a rim 170 for engagement and penetration into the surface 22 of the rod 21 in certain embodiments of the invention. The closure top 18 may further include a cannulation through bore (not shown) extending along a central axis thereof and through the top and bottom surfaces thereof. Such a through bore provides a passage through the closure 18 interior for a length of wire (not shown) inserted therein to provide a guide for insertion of the closure top into the receiver arms 60A and B.

Figure 25:
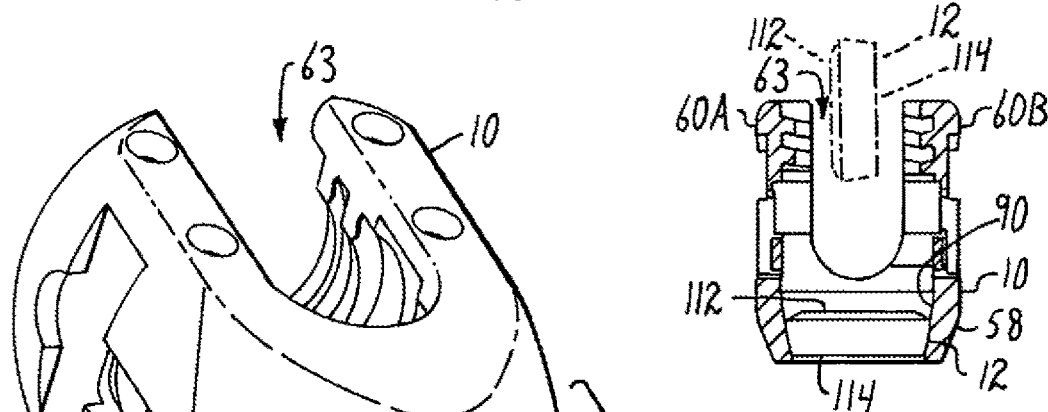
FIG. 25 is a front elevational view of the receiver and retainer of FIG. 1 with portions broken away to show the detail thereof and further showing a stage of assembly of the retainer in phantom.
Figure 26:
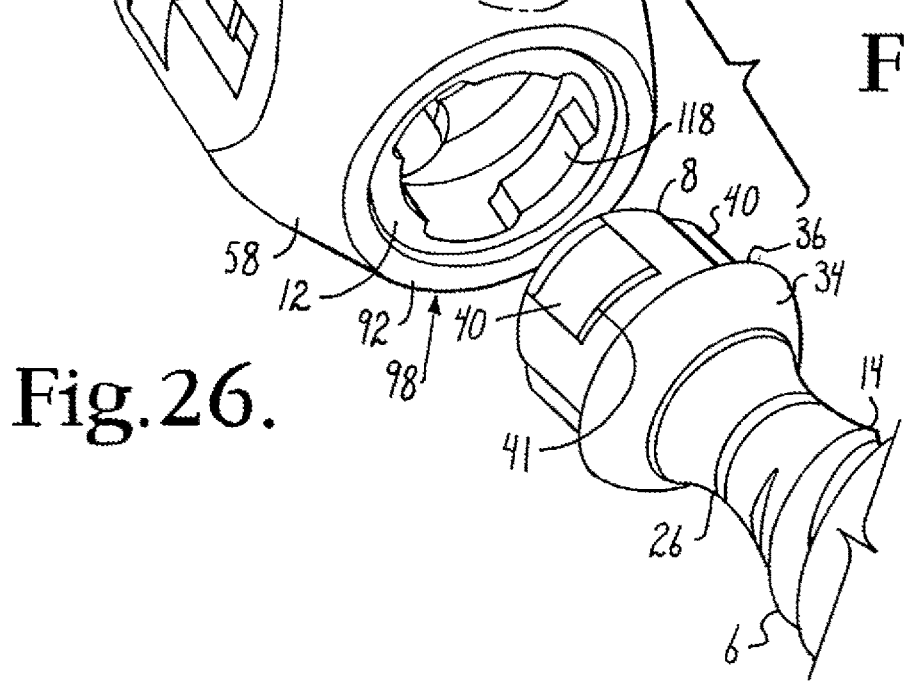
FIG. 26 is an enlarged and partial perspective view of the receiver, retainer and shank of FIG. 1 shown in an early stage of assembly.

Preferably, the shank 4, receiver 10, the retainer 12 and the compression insert 14 are assembled at a factory setting that includes tooling for holding and alignment of the component pieces and compressing arm portions of the insert 14. Assembly of the shank 4, the receiver 10, the retainer 12 and the compression insert 14 is shown in rigs. 25-34*b*. With particular reference to FIG. 25, the ring-like retainer 12 is typically first inserted or top-loaded through the opening 63 with the top 112 and bottom 114 surfaces aligned with the receiver axis B within the receiver U-shaped channel 62 and then into the cavity 90 to dispose the structure 12 within the receiver base 58. Then, the retainer structure 12 is rotated approximately 90 degrees so as to be coaxial with the receiver 10 and then seated in sliding engagement with the seating surface 96 of the receiver 10. With reference to FIGS. 26-28, the shank capture structure 8 is then inserted or bottom-loaded into the receiver 10 through the opening 98. The retainer structure 12, now disposed in the receiver 10 is coaxially aligned with the shank capture structure 8 so that the camming lugs 40 are received by the retainer 12 and moved between and through the camming shelves 118 until the bottom surface 114 of the retainer 12 engages the surface 36 of the shank upper portion 8. The retainer 12 is then partially rotated about the axis A of the shank 4 until the retainer shelves 118 are received in the cam track formed by the shank surface 36 and the shank projection camming or sloped surface 41. With reference to FIGS. 27 and 28, as the retainer 12 is rotated, the shank projection bottom surface 41 frictionally engages the ramped surface 120 of the camming shelf 118, creating a press fit between the surfaces and frictionally locking the retainer 12 between the lugs or projections 40 and the shank upper portion 8 seat 36, the retainer 12 now in fixed coaxial relationship with the shank 4. Preferably, the shank 4 and or the retainer 12 are partially rotated to fully mate such structures at a factory setting that includes tooling for holding and precisely rotating the shank 4 and/or the retainer 12 until locking frictional engagement therebetween is accomplished. Although not shown, it is noted that the retainer structure 12 may also have tooling features, such as a pair of small apertures so that the retainer 12 is also securely held during the rotation with respect to the shank 4. Permanent, rigid engagement of the capture structure 8 to the retainer structure 12 may be further supported by the use of adhesive, a spot weld, a deformation, or the like. At this time both the shank 4 and the retainer 12 are in loose, rotatable and swivelable engagement with the receiver 10, while the shank upper portion 8 and the lower aperture or neck 97 of the receiver 10 cooperate to maintain the shank body 6 in swivelable relation with the receiver 10. Only the retainer 12 is in slidable engagement with the receiver spherical seating surface 96. The shank upper end 44 and the shank body 6 are in spaced relation with the receiver 10. The shank body 6 can be rotated through a substantial angular rotation relative to the receiver 10, both from side to side and from front to rear so as to substantially provide a universal or ball joint.

With reference to FIGS. 29-34b, the compression insert 14 is downloaded into the receiver 10 through the upper opening 63 with the insert bottom surface 153 facing the receiver arm top surfaces 69 and the insert arms 135 located between the receiver arms 60A and 60B. The insert 14 is lowered toward the channel seat 64 until the insert 14 is located below the surface run-put feature 76 of the guide and advancement structure 68 and the spherical surface 132 engages the domed surface 44 of the shank 4. Thereafter, the insert 14 is rotated in a clockwise manner as indicated by the arrow CL in FIG. 30 until the stop structures 104 of the insert 14 abut against the wall 102 of the recess stop 100 located on the receiver arms 60A and 608 (see FIG. 31). During such rotation, the upper projections 146 also engage the receiver cylindrical surface 77, compressing the outer arm portions 155 toward the inner arm portions 154 to provide a slidable friction fit between the insert 14 and the receiver 10 at the surface 77. At this time, the insert 14 engages the shank upper portion 8 at the surface 44 in a manner that allows for pivoting of the shank with respect to the receiver 10 with effort, thus a frictional fit that advantageously allows for setting a desired angle of the shank 4 with respect to the receiver 10, that may be adjusted, but is not otherwise floppy or loosely movable. The surface 76 of the receiver prohibits the insert 14 from moving upwardly away from the shank surface 44. With further reference to FIG. 31, at this time, the spring tabs 75 may be pressed inwardly into the insert recesses 160, preventing counter-clockwise movement of the insert 14 with respect to the receiver 10. FIG. 34a best illustrates the position of the insert 14 with respect to the receiver 10 prior to implanting of the shank body 6 into the vertebra 13.

Figure 32:
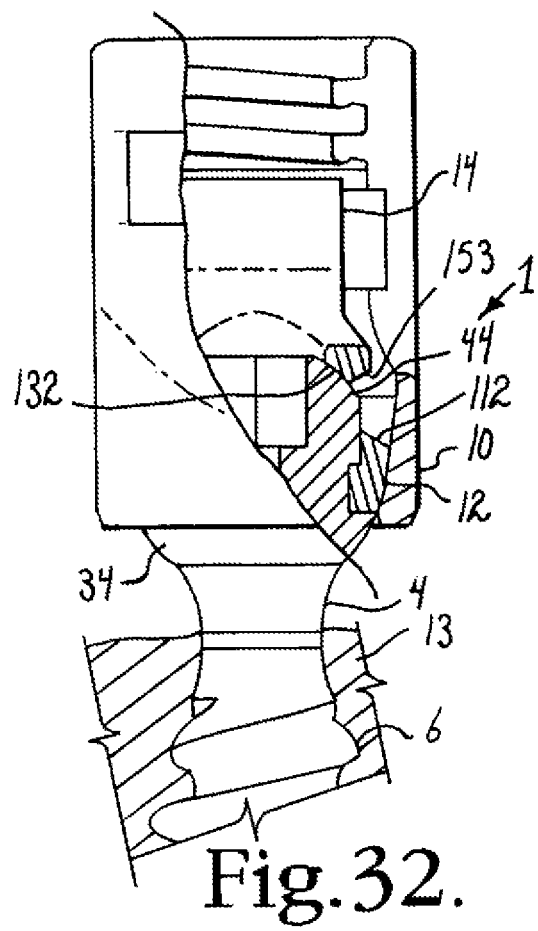
FIG. 32 is a reduced side elevational view of the receiver, retainer, shank and insert of FIG. 31 with portions broken away to show the detail thereof.
Figure 33:
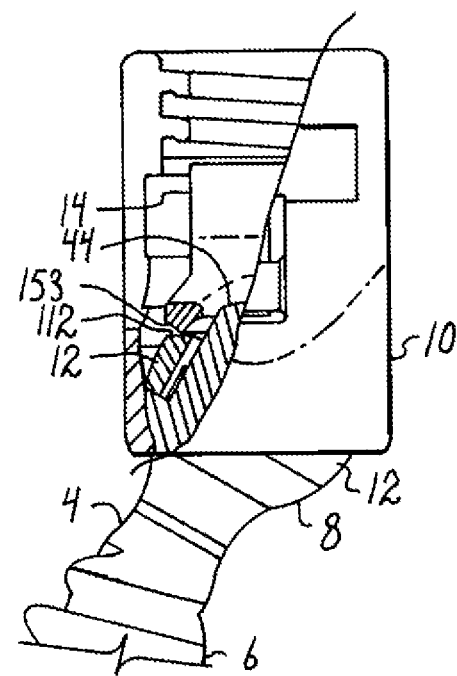
FIG. 33 is a reduced side elevational view, with portions broken away, similar to FIG. 32, further showing the shank pivoted at an angle with respect to the receiver.

With reference to FIG. 32, the assembly 1 made up of the assembled shank 4, receiver 10, retainer 12 and compression insert 14 is screwed into a bone, such as the vertebra 13, by rotation of the shank 4 using a suitable driving tool (not shown) that operably drives and rotates the shank body 6 by engagement thereof at the internal drive 50. Specifically, the vertebra 13 may be pre-drilled to minimize stressing the bone and have a guide wire (not shown) inserted therein to provide a guide for the placement and angle of the shank 4 with respect to the vertebra. A further tap hole may be made using a tap with the guide wire as a guide. Then, the bone screw assembly is threaded onto the guide wire utilizing the cannulation bore 51 by first threading the wire into the opening at the bottom 28 and then out of the top opening at the drive feature 50. The shank 4 is then driven into the vertebra using the wire as a placement guide. It is foreseen that the shank and other bone screw assembly parts, the rod 21 (also having a central lumen in some embodiments) and the closure top 18 (also with a central bore) can be inserted in a percutaneous or minimally invasive surgical manner, utilizing guide wires. At this time, the receiver 10 may be articulated to a desired position with respect to the shank 4 as shown, for example, in FIG. 33.

Figure 35:
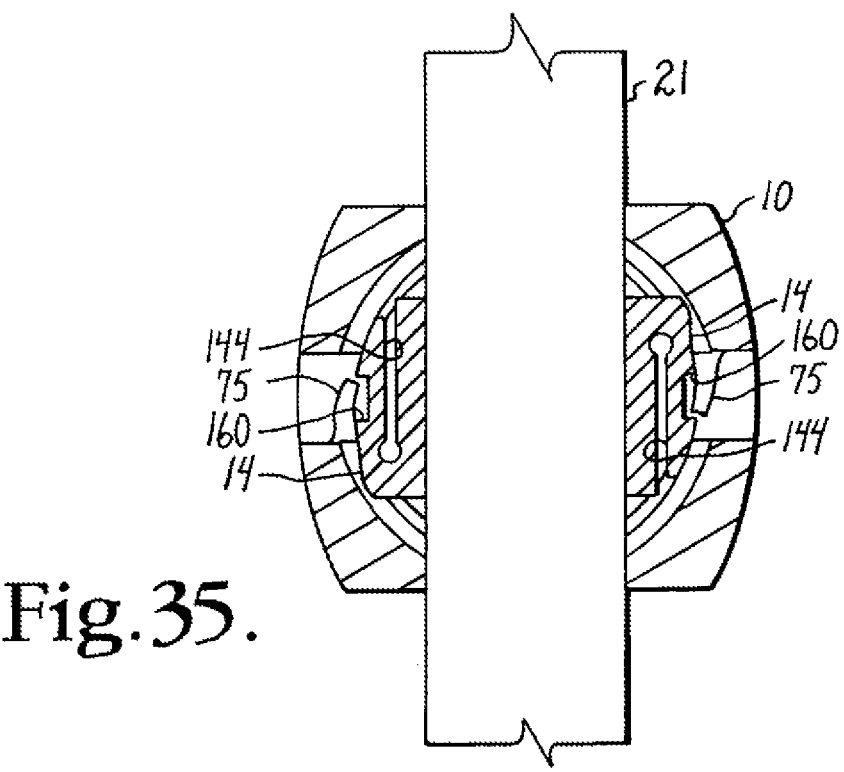
FIG. 35 is a top plan view of the assembly of FIG. 34, with portions broken away to show the detail thereof and further shown with the rod of FIG. 1, the insert being pressable downwardly into the second or locked position by the rod.

With reference to FIGS. 34a, 34b and also FIG. 35, at this time, the insert 14 may be placed into a fixed or locked position with respect to the receiver 10 by pressing the insert 14 axially downwardly against the shank top surface 44. This may be done by pressing the rod 35 into the insert 14 as shown in FIG. 35 or by tooling (not shown) that lowers the insert 14 to a location out of engagement with the cylindrical surface 77 as shown in FIG. 34b. At such time, the outer arm portion 155 resiliently moves or springs back toward a neutral position, and such action puts the outer arm portion 155 into a full, frictional engagement with the lower receiver surface 86, locking the insert 14 against the shank upper portion 8, the shank 4 no longer movable with respect to the receiver 10. At this time the surgeon may make other adjustments in the rod 21 or other longitudinal connection assembly components with confidence that the shank 4 and the receiver 10 of the assembly 1 is fully locked into a desired angular position. If, however, an adjustment is desired, tools (not shown) may be inserted into the receiver aperture 74 and the insert outer arm portion 155 may be compressed inwardly radially toward the axis B, loosening the insert 14 from the receiver cylindrical surface 86, and thus loosening engagement between the insert surface 132 and the shank upper portion surface 44.

Figure 36:
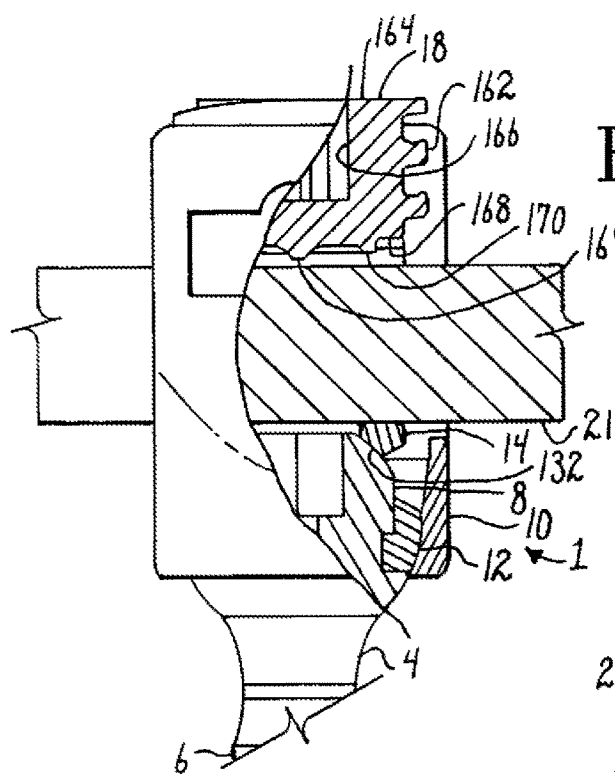
FIG. 36 is an enlarged and partial side elevational view of the assembly of FIG. 35, further showing the closure top of FIG. 1 in a stage of assembly with the receiver with portions broken away to show the detail thereof.
Figure 37:
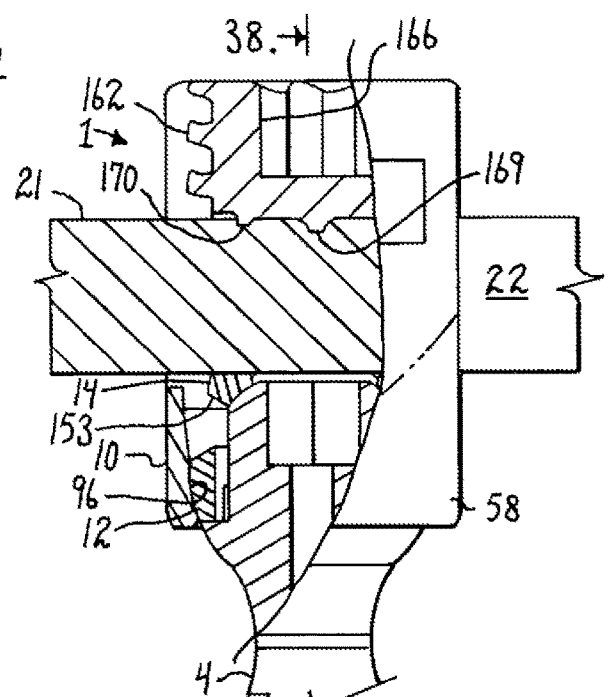
FIG. 37 is an enlarged and partial side elevational view of the assembly of FIG. 36 with portions broken away to show the detail thereof and showing the closure top engaging the rod.
Figure 38:
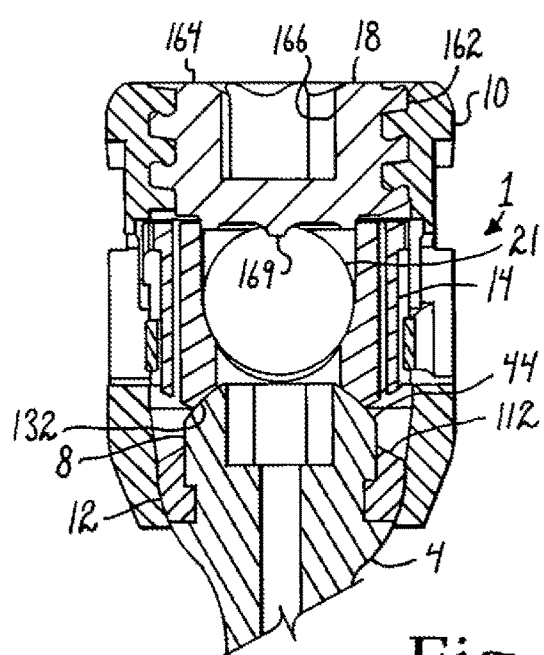
FIG. 38 is an enlarged and partial cross-sectional view taken along the line 38-38 of FIG. 37.

With reference to FIGS. 36-38, the rod 21 is eventually positioned in an open or percutaneous manner in cooperation with the at least two bone screw assemblies i. The closure structure 18 is then inserted into and advanced between the arms 60A and 60B of each of the receivers 10. The closure structure 18 is rotated, using a tool engaged with the inner drive 166 until a selected pressure is reached at which point the rod 21 engages the insert 14, biasing the insert spherical surface 132 against the shank spherical surface 44.

As the closure structure 18 rotates and moves downwardly into the respective receiver 10, the point 169 and rim 170 engage and penetrate the rod surface 22, the closure structure 18 pressing downwardly against and biasing the rod 21 into engagement with the insert 14 that urges the shank upper portion 8 toward the retainer 12 and into locking engagement therewith, the retainer 12 frictionally abutting the surface 96. For example, about 80 to about 120 inch pounds of torque on the closure top may be applied for fixing the bone screw shank 6 with respect to the receiver 10.

If removal of the rod 21 from any of the bone screw assemblies 1 is necessary, or if it is desired to release the rod 21 at a particular location, disassembly is accomplished by using the driving tool (not shown) that mates with the internal drive 166 on the closure structure 18 to rotate and remove such closure structure from the cooperating receiver 10. Disassembly is then accomplished in reverse order to the procedure described previously herein for assembly.

With reference to FIGS. 39-41, the assembly 1 is illustrated with an alternative rod 21' and an alternative closure top 18', thus the resulting assembly is identified as an assembly 1'. The rod 21' is substantially similar to the rod 21 in size and shape. However, the rod 21' is made from a deformable material, illustrated as a plastic material. The closure top 18' is substantially similar to the top 18 with the exception that the top 18' includes an outer annular flat bottom surface 168' adjacent to an otherwise curved bottom that further includes a central rounded point or projection 169' located on a spherical or domed shape surface 170'. As best shown in FIG. 41, when assembled, the closure top surface 168' engages the insert arm top surfaces 140, pressing the insert 14 in a downward direction toward the shank upper portion 8, providing locking of the insert 14 against the shank top surface 44 independent of any engagement between the closure top 18' and the rod 21'. The closure top surfaces 169' and 170' engage and penetrate the deformable rod 21'.

Figure 42:
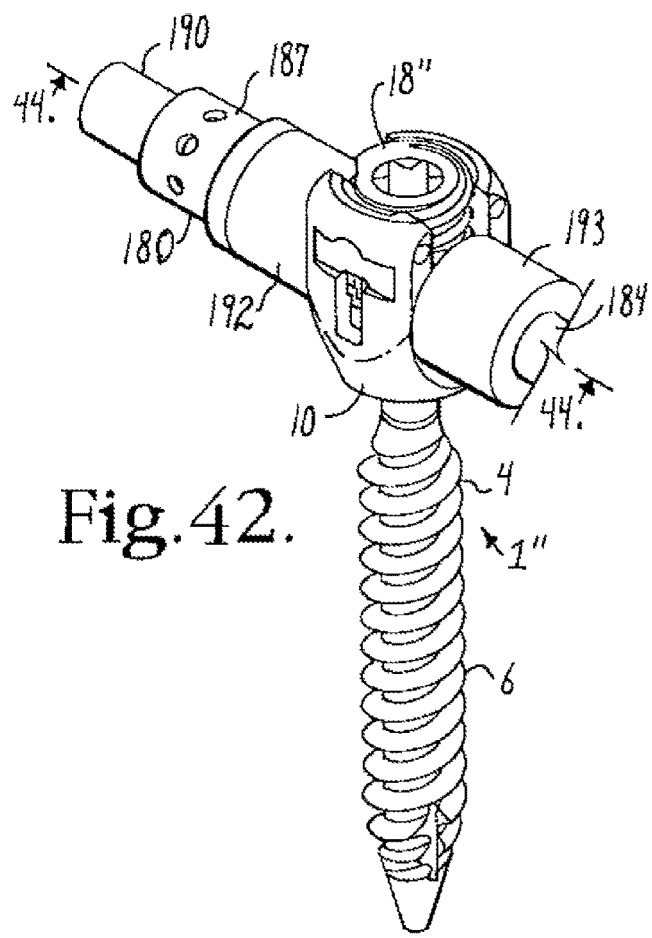
FIG. 42 is a reduced and partial perspective view showing the assembled receiver, shank, retainer and insert of FIGS. 32-34 with a cord, first and second spacers located on either side of the receiver, a threaded connecter, a rod and a closure top configured for slidable engagement with the cord.
Figure 43:
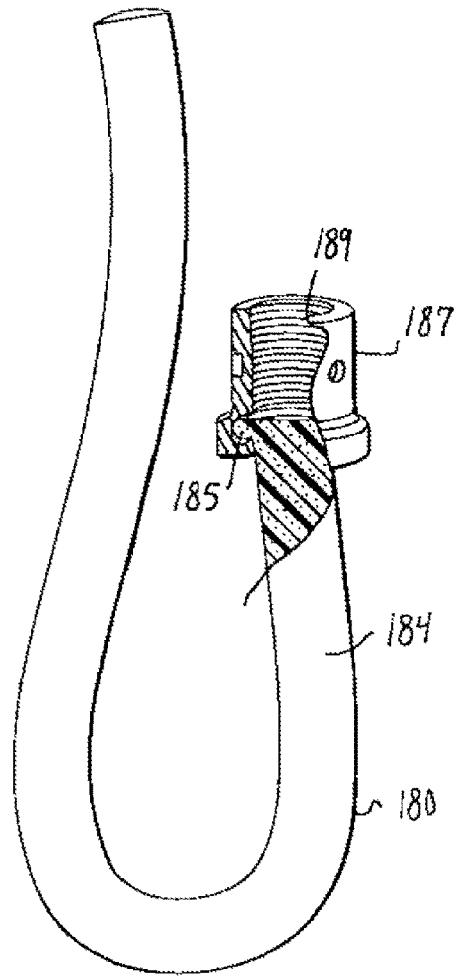
FIG. 43 is a perspective view of the cord and connector of FIG. 42 with portions broken away to show the detail thereof.
Figure 44:
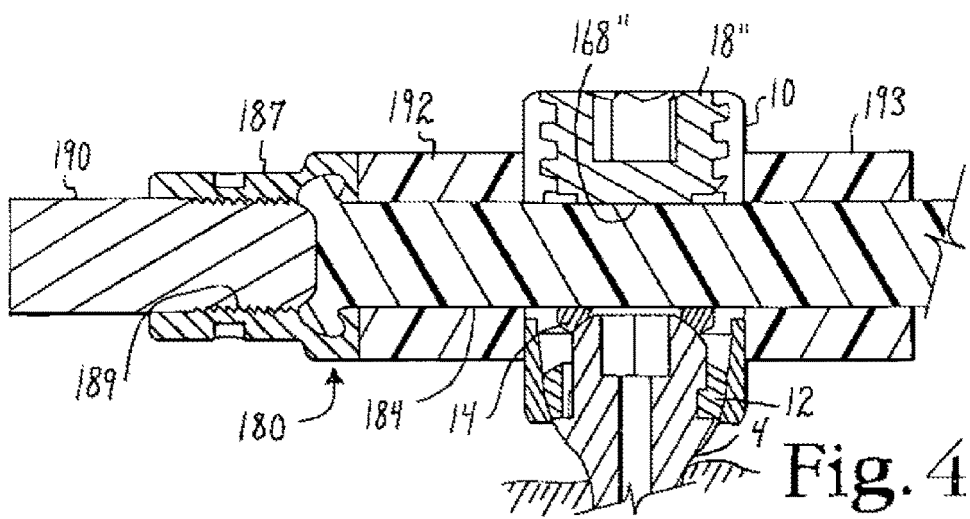
FIG. 44 is an enlarged and partial cross-sectional view taken along the line 44-44 of FIG. 42.

With reference to FIGS. 42-46, the assembly 1 of the invention is shown with alternative closure tops 18" and 18'" as well as with a cord/cord coupler combination 180 and a cord 184. With particular reference to FIGS. 42-44, he assembly 1" is identical to the assembly 1 previously described herein with the exception of the rod 21 is replaced by the cord/cord coupler combination 180 and the closure 18 is replaced by the closure 18". The cord/cord coupler combination 180 further includes a cord 184 with a lip 185 that is fixed within a coupler 187 that further includes inner threads 189 for attaching to a hard rod 190. The illustrated assembly further includes spacers 192 and 193 that may be compressible or not. In operation, the cord 184 is placed in tension. The closure top 18" includes a planar bottom surface 168" sized and shaped to abut against the insert 14 top surface 140 as illustrated in FIG. 41 with respect to the assembly 1', providing independent locking of the shank 4 with respect to the receiver 10. Alternatively, sufficient locking of the bone screw 1" may be provided by the insert 14 outer arm portions pressing against the cylindrical surface 86 of the receiver 10 as illustrated in FIG. 34b with respect to the assembly 1. The bottom surface 168" of the closure 18" allows for the cord 180 to slide with respect to the receiver 10, the cord being fixed to the rod 190 at the coupler 187. In such an arrangement, the cord 180 is also fixed to another bone screw 1 (not shown) or fixed to a fixing or blocking structure (not shown) engaging the cord 184 at a location opposite the spacer 193 or other cooperating bone screws.

Figure 45:
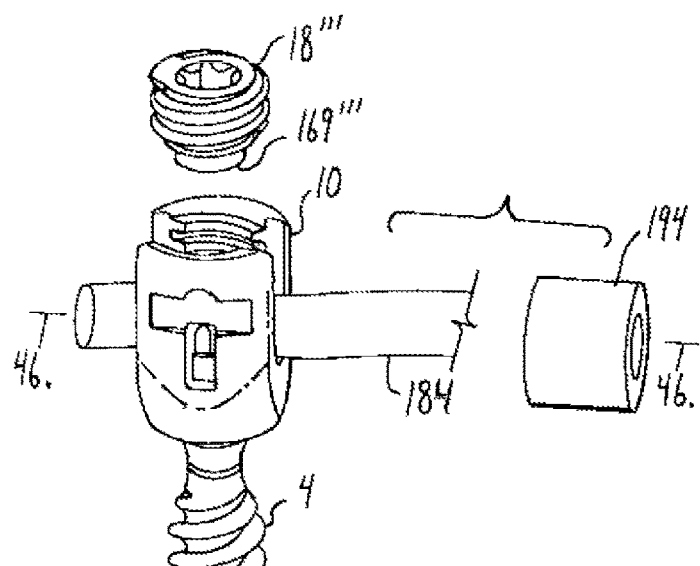
FIG. 45 is a reduced and partial, partially exploded view, showing the assembled receiver, shank, retainer and insert of FIGS. 32-34 with a cord, a spacer and a closure top configured for fixed engagement with the cord.
Figure 46:
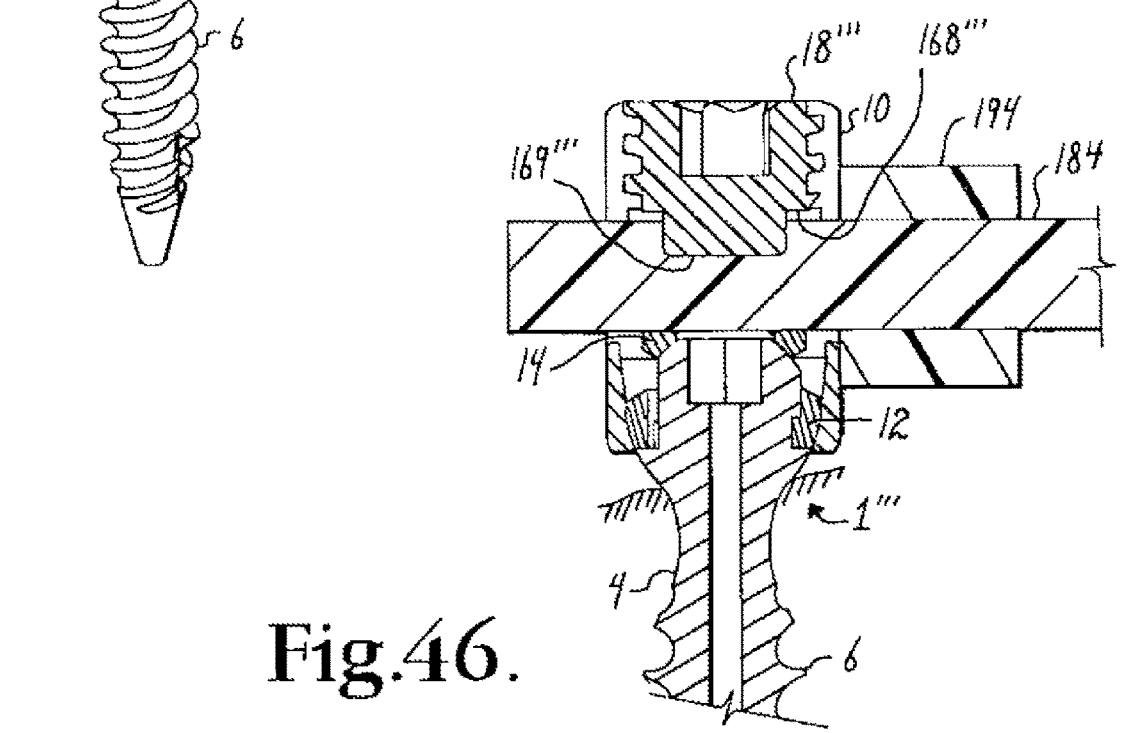
FIG. 46 is an enlarged and partial cross-sectional view, taken along the line 46-46 of FIG. 45 and showing the spacer and closure top in an assembled position.

With reference to FIGS. 45 and 46, the assembly 1'" is identical to the assembly 1 with the exception that the rod 21 is replaced by the cord 184 and the closure 18 is replaced by the closure 18'". The closure 18'" includes a planar bottom rim 168'" as well as an extension or protrusion 169'" that engages and penetrates the cord 184, holding the cord 184 in fixed engagement with the bone screw assembly 1'". Also illustrated is a spacer 194 that may be compressible or not. The cord 184 is preferably in tension. For example, the assembly 1'" may be used in combination with the assembly 1" shown in FIGS. 42-44 with the spacer 193 located between the bone screw assemblies 1" and 1'", the cord 180 replacing the cord 184. Thus, the cord 180 would be held in tension between the coupler 187 and the bone screw closure 169'".

With reference to FIGS. 47-63, an alternative embodiment of a bone anchor assembly according to the invention, generally 201 is illustrated. The assembly 201 includes a shank 204 having a shank body 206 and an upper portion 208, a receiver 210, a cam retainer 212 and a compression or pressure insert 214. The assembly 201 is substantially similar to the assembly 1 with the exception of certain features of the receiver 210 and the insert 214 as will be described in detail below. Unlike the insert 14, the insert 214 includes a top surface, rather than an outer or side surface that frictionally engages the receiver 210 to place the insert 214 into frictional engagement with the shank upper portion 208 prior to placement of a rod 21 or other longitudinal connecting member into the receiver 210. Somewhat similar to the insert 14, the insert 214 includes an outer surface that engages a cylindrical surface of the receiver 210 to place the insert 214 into locking engagement with the shank upper portion 208 prior to ultimate locking with a closure top (not shown) that may be the closure top 18, 18', 18" or 18'" previously described herein with respect to the assemblies 1, 1', 1" and 1'", the closure ton chosen based upon the type of rod, cord or other longitudinal connecting member being placed within the receiver 210. Similar to the insert 14, the insert 214 may be compressed or squeezed to release locking engagement with the receiver 210 and the shank upper portion 208. The insert 214 advantageously provides such a release-able locking engagement without the key hole slot feature of the insert 14 as will be described in greater detail below.

Figure 47:
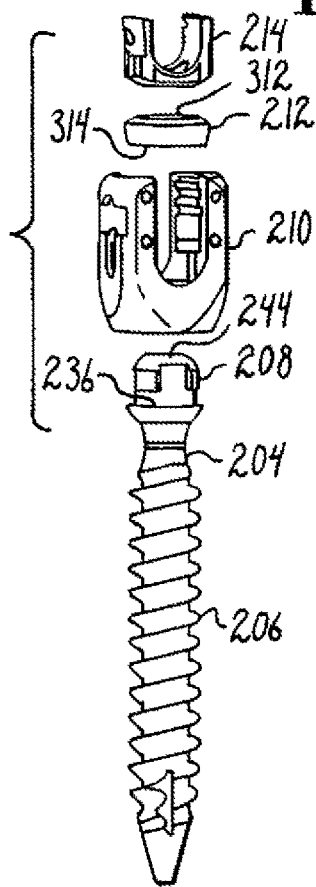
FIG. 47 is an exploded perspective view of an alternative embodiment of a polyaxial bone screw assembly according to the present invention including a shank, a receiver, a retainer and a compression insert.
Figure 48:
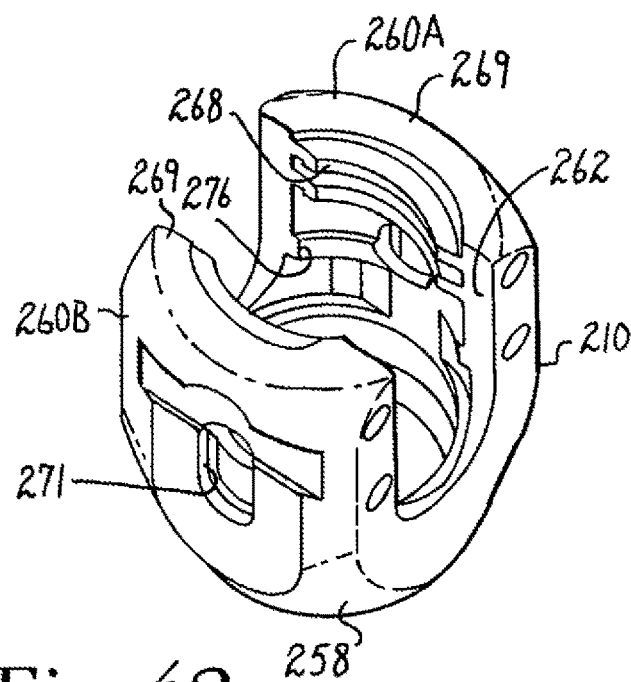
FIG. 48 is an enlarged perspective view of the receiver of FIG. 47.
Figure 49:
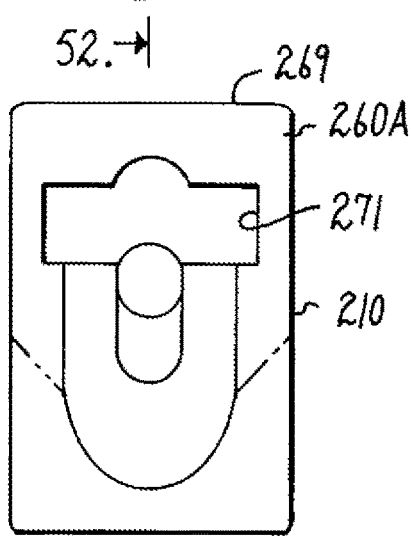
FIG. 49 is an enlarged side elevational view of the receiver of FIG. 47.
Figure 50:
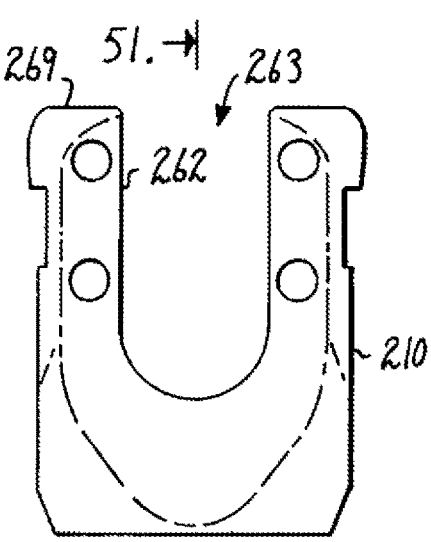
FIG. 50 is an enlarged front elevational view of the receiver of FIG. 47.
Figure 51:
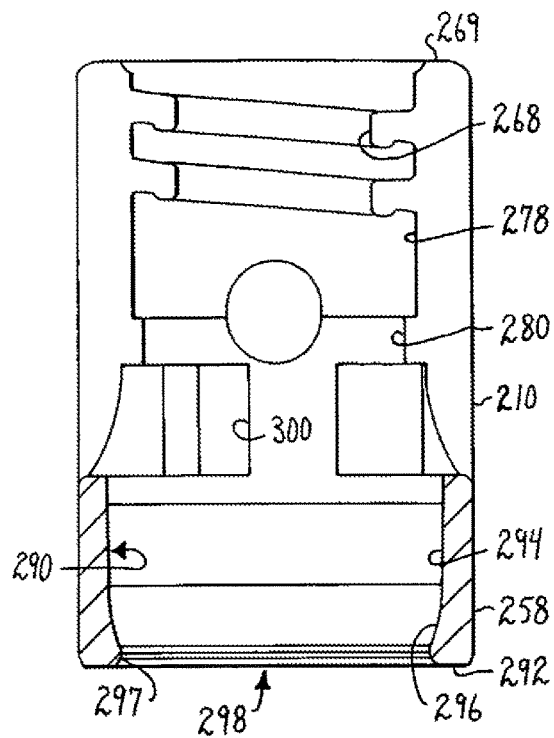
FIG. 51 is an enlarged cross-sectional view taken along the line 51-51 of FIG. 50.
Figure 52:
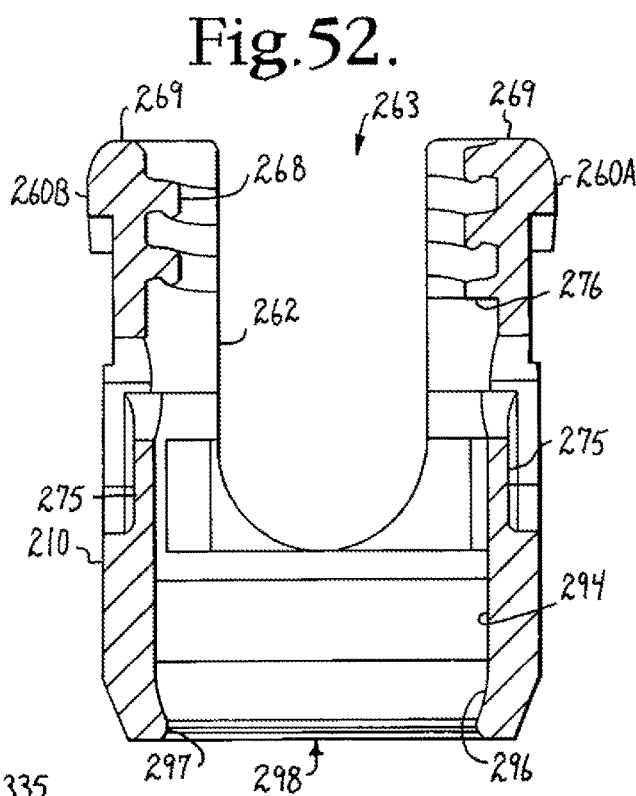
FIG. 52 is an enlarged cross-sectional view taken along the line 52-52 of FIG. 49.
Figure 53:
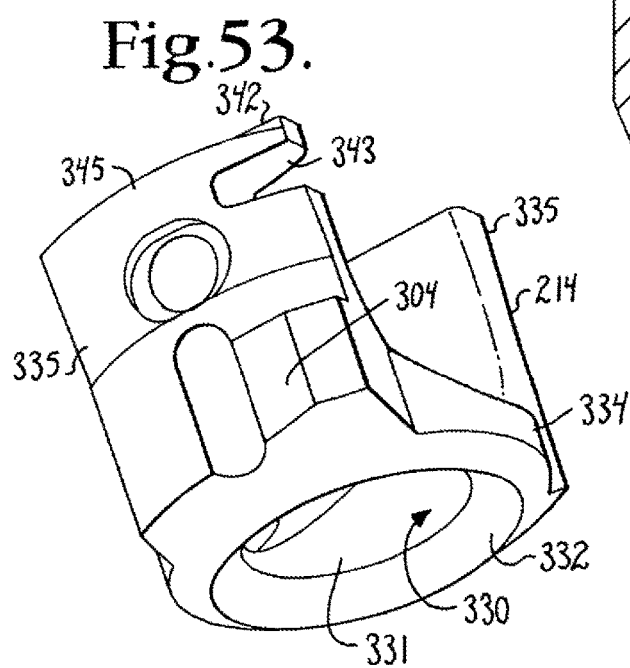
FIG. 53 is an enlarged perspective view of the insert of FIG. 47.
Figure 62:
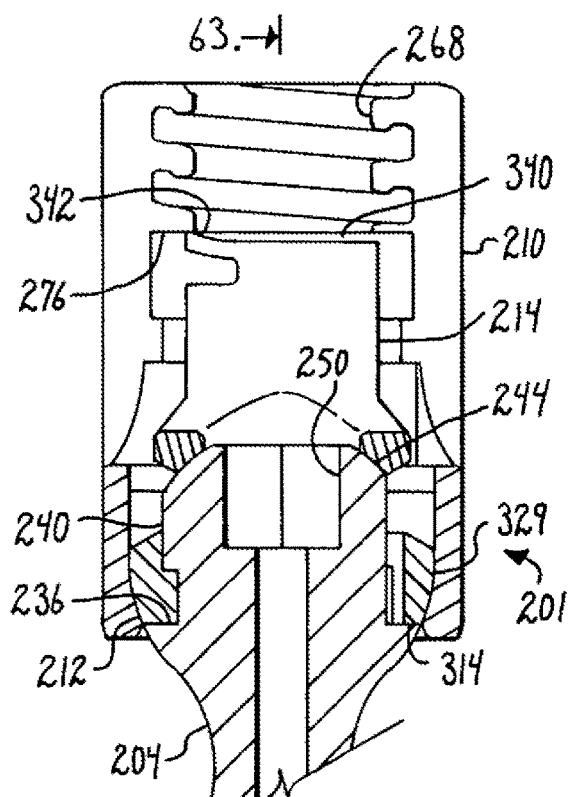
FIG. 62 is a reduced and partial cross-sectional view taken along the line 62-62 of FIG. 61.
Figure 63:
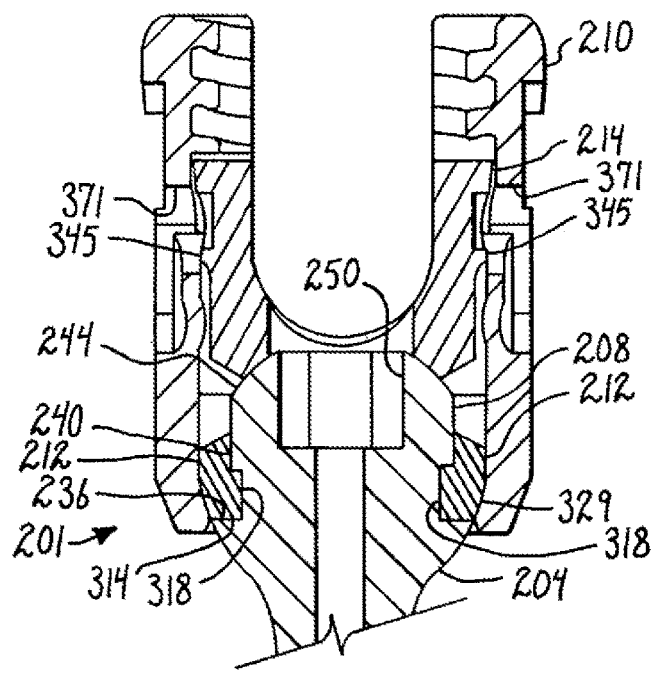
FIG. 63 is a partial cross-sectional view taken along the line 63-63 of FIG. 62.

With particular reference to FIGS. 47, 62 and 63, the shank 204 is identical or substantially similar to the shank 4 of the assembly 1 and therefore, among other things, includes a spherical surface 234, a retainer seat 236, three cam lugs or projections 240, a domed top 244, and an internal drive feature 250, the same or similar to the respective spherical surface 34, retainer seat 36, cam lugs 40, domed top 44 and internal drive 50 previously discussed herein with respect to the shank 4. Similarly, the retainer 212 includes, among other things, a top 312, bottom 314, cam shelves 318 and outer spherical surface 329 that are the same or substantially similar to the respective top 112, bottom 114, cam shelves 118 and outer spherical surface 129 of the retainer 12 previously described herein with respect to the assembly 1. The shank 204 and the retainer 212 are assembled within the receiver 210 in a manner the same or substantially similar to that described previously herein with respect to the shank 4, retainer 12 and receiver 10 of the assembly 1.

Although substantially similar to the receiver 10, the receiver 210 includes some features that are different than the receiver 10 and thus shall be described more fully herein. The receiver 210 includes a base 258, arms 260A and 260B, a U-shaped channel 262, a channel upper opening 263, channel lower seat 264, a guide and advancement structure 268, and arm top surfaces 269, that are the same or substantially similar to the respective base 58, arms 60A and 60B, U-shaped channel 62, channel upper opening 63, channel lower seat 64, guide and advancement structure 68, and arm top surfaces 69 previously described herein with respect to the receiver 10. The receiver 210 further includes a T-shaped tool engagement feature 271 somewhat similar to the feature 71 of the receiver 10. However, The feature 271 further includes a thin crimp wall 275 that provides alignment for the insert 214 similar to the tabs 75 of the receiver 10. The crimp wall 275 is simply pressed inwardly radially toward the insert 214 to prohibit counterclockwise rotation of the insert 214 with respect to the receiver 210. Similar to the receiver 10, the receiver 210 includes a bottom abutment surface 276 of the guide and advancement run-out located on the arm 260A, the surface 276 frictionally engaging a top surface of the insert 214 as will be described more fully below. Located beneath the surface 276 is a discontinuous cylindrical surface 278 that communicates with another discontinuous cylindrical surface 280 having a diameter smaller than a diameter of the surface 278, the surface 280 cooperating with the insert 214 to lock the insert against the shank upper portion 208 as will be described more fully below. A receive cavity, generally 290 includes an upper cylindrical or slightly conical surface 294 and a spherical seating surface 296 for sliding and ultimate frictional mating with the retainer spherical surface 329. The receiver 210 further includes a lower neck 297 forming an opening 298 at a bottom surface 292 of the receiver 210. Formed in the arm cylindrical surface 280 is a pocket or stop 300 for receiving a projection 304 of the insert 214 to prohibit clockwise movement of the insert 214 with respect to the receiver 210 and thus provide alignment between the insert 214 and the receiver 210 similar to what was previously described herein with respect to the insert 14 and the receiver 10.

Figure 64:
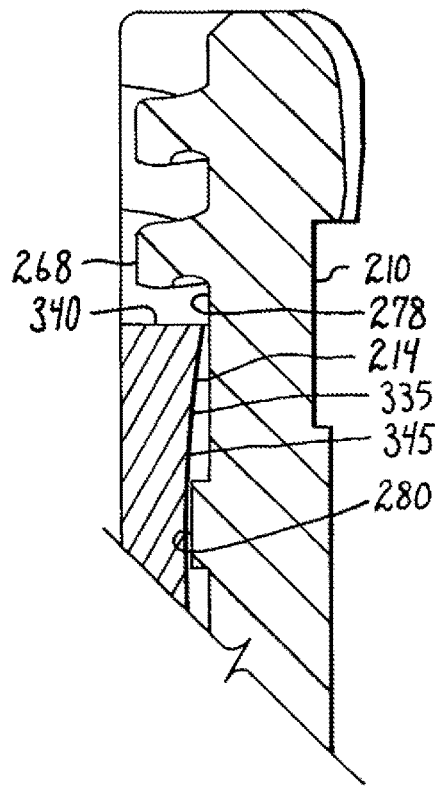
FIG. 64 is an enlarged and partial front elevational view of the assembly of FIG. 61, with portions broken away to show the detail of an initial surface engagement between the insert and receiver.

The insert 214 includes a bore, 330, an inner cylindrical surface 331, an inner spherical surface 332, a substantially cylindrical body 334, upstanding arms 335, a u-shaped channel 336, a channel seat 338 and arm top surfaces 340 substantially similar to the respective bore, 130, inner cylindrical surface 131, inner spherical surface 132, substantially cylindrical body 134, upstanding arms 135, u-shaped channel 136, channel seat 138 and arm top surfaces 140 previously described herein with respect to the insert 14. However, the insert 214 does not include the key-hole slot feature of the insert 214. Instead, at least one or both of the top surfaces 240 includes an upwardly sloping surface feature 342 spaced from a notch 343 formed in the insert arm 335. Thus, the notch 343 may be pressed downwardly toward the body 334. FIG. 55 illustrates an embodiment wherein both surfaces 240 include the surface feature 342, the second feature shown in phantom as 342'. As best illustrated in FIG. 62, the surface 342 engages the receiver surface 276 to hold the insert 214 against the shank upper surface 244 after assembly therewith, so that a friction-fit, non-floppy engagement between the insert 214 and the shank top 208 allows for placement of the angle of the shank 204 with respect to the receiver 210 during surgery and prior to the rod or other connecting member being placed in the receiver 210. Furthermore, the arms 335 include upper portions 345 that flare outwardly and are sized and shaped to cooperate with the surface 280 of the receiver 210 (see FIG. 64) for tight frictional, locking fit between the insert 214 and the shank upper portion 208 when the insert 214 is pushed downwardly toward the receiver base, either by a rod or by a tool. Such locking may be released by a inserting a tool (not shown) in the tool engagement feature 371 and pressing the insert 214 radially inwardly.

The insert 214 is loaded into the receiver 210 in a manner similar to that described above with respect to the insert 14 and the receiver 10 of the assembly 1. The assembly 201 is thereafter fitted with a rod 21 or other longitudinal connecting member and a closure top 18 or cooperating top as described above with respect to the assembly 1.

Figure 65:
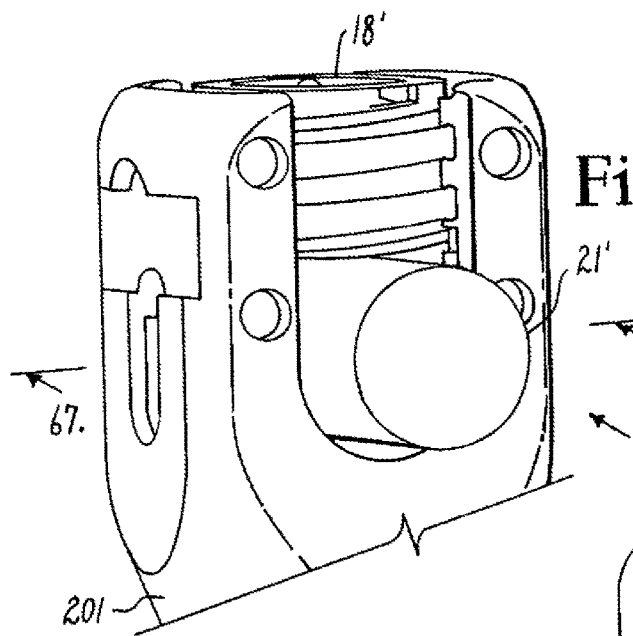
FIG. 65 is an enlarged and partial perspective view of the assembly of FIG. 47 shown assembled with a deformable rod and a closure top.
Figure 66:
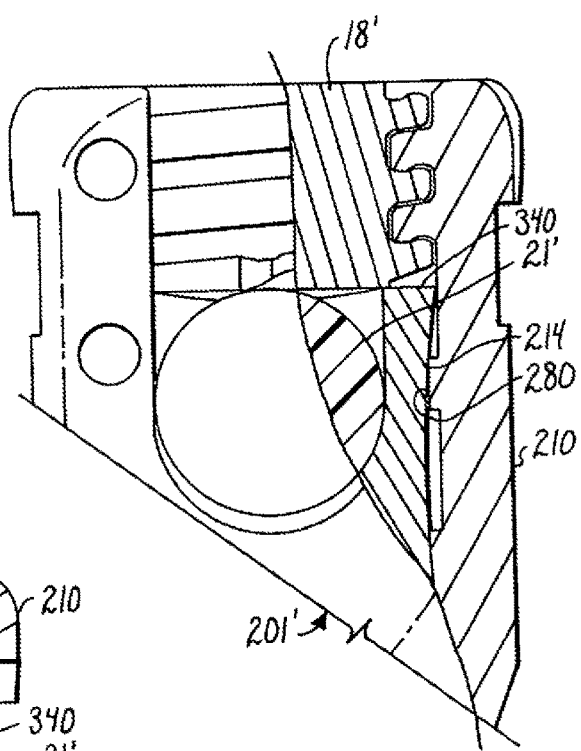
FIG. 66 is an enlarged and partial front elevational view of the assembly of FIG. 65 with portions broken away to show the detail thereof.
Figure 67:
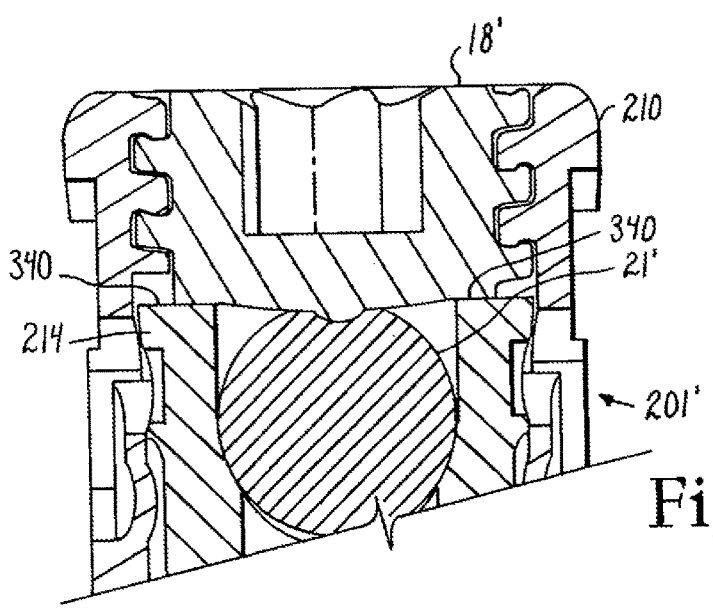
FIG. 67 is an enlarged and partial cross-sectional view taken along the line 67-67 of FIG. 65.

With reference to FIGS. 65-67, the assembly 201 is shown with the deformable rod 21' and the closure top 18' previously described herein. Thus, the resulting assembly is identified as 210'. As illustrated, the closure 18' presses and locks down upon the insert 214 at the surface 340, independently locking the assembly 201 when the assembly is used to capture the deformable rod 21'. Further independent locking is provided by the insert 214 pressing against the receiver surface 280.

It is to be understood that while certain forms of the present invention have been illustrated and described herein, it is not to be limited to the specific forms or arrangement of parts described and shown.

What is claimed is:

1. A pivotal bone anchor assembly for securing a longitudinal connecting member to a bone of a patient via a closure, the pivotal bone anchor assembly comprising:
   a receiver comprising a base portion defining a lower portion of a central bore centered about a vertical centerline axis and communicating with a bottom surface of the base portion through a bottom opening, and an integral upper portion defining a channel configured to receive the longitudinal connecting member, the central bore extending upward from the bottom opening through the channel to a top of the upper portion and including a helically wound guide and advance structure adjacent the top of the upper portion, an integral non-threaded downward-facing surface below the helically wound guide and advance structure, and a seating surface adjacent the bottom opening;
   a shank comprising a head portion and an anchor portion opposite the head portion configured for attachment to the bone, the head portion being positionable within the lower portion of the central bore with the shank extending downwardly through the bottom opening;
   a compression insert comprising a lower insert portion defining a center opening and an upper insert portion having at least one slot formed therein to define at least one resiliently downwardly compressible structure extending over the at least one slot, the compression insert being positionable within the central bore of the receiver with the at least one resiliently downwardly compressible structure being engageable with the downward-facing surface,
   wherein when the head portion of the shank and the compression insert are positioned together in the central bore of the receiver, the engagement between the at least one resiliently downwardly compressible structure and the downward-facing surface is configured to provide an axially directed resilient biasing force for a pre-lock friction fit of the pivotal bone anchor assembly prior to securing the longitudinal connecting member in the open channel with the closure.

2. The pivotal bone anchor assembly of claim 1, wherein the compression insert further comprises an upwardly-facing partial cylindrical surface alignable with the channel of the receiver and configured to receive the longitudinal connecting member.

3. The pivotal bone anchor assembly of claim 2,
wherein the upper insert portion further comprises a pair of insert arms extending upward from the lower insert portion to define the partial cylindrical surface therebetween, and
wherein the at least one slot further comprises a pair of notches formed into the pair of insert arms to define a pair of resiliently downwardly compressible structures opposite from one another across the center opening of the compression insert.

4. The pivotal bone anchor assembly of claim 2, wherein the compression insert is configured for positioning into the central bore of the receiver in a first position and then for rotation about the vertical centerline axis toward a second position with the at least one resiliently downwardly compressible structure being rotated into engagement with the downward-facing surface of the central bore.

5. The pivotal bone anchor assembly of claim 4, further comprising at least one inner pocket formed into the central bore of the receiver between the at least one downward facing surface and the seating surface and at least one protuberant interference structure projecting radially outward from a side of the compression insert,
wherein the at least one inner pocket is configured to receive the at least one protuberant interference structure upon rotation of the compression insert about the vertical centerline axis into the second position so as to inhibit further rotation of the compression insert with respect to the receiver in at least one direction.

6. The pivotal bone anchor assembly of claim 1,
wherein the head portion of the shank further comprises a spherical upper surface, and
wherein the lower insert portion further comprises a downwardly-facing spherical inner surface configured to directly engage the spherical upper surface of the head portion of the shank.

7. The pivotal bone anchor assembly of claim 1, wherein the compression insert is downloadable into the central bore through the upper portion of the receiver.

8. The pivotal bone anchor assembly of claim 1, wherein the head portion of the shank is uploadable into the lower portion of the central bore through the bottom opening of the receiver.

9. The pivotal bone anchor assembly of claim 1 and further comprising a retainer configured for positioning within the lower portion of the central bore, the retainer having a lower outer surface configured to engage the seating surface of the axial bore and an inner surface configured to capture and hold the head portion of the shank within the base portion of the receiver.

10. The pivotal bone anchor assembly of claim 9, where the retainer is positionable within the lower portion of the central bore prior to the head portion of the shank.

11. The pivotal bone anchor assembly of claim 9,
wherein the seating surface of the central bore further comprises a spherical seating surface adjacent the bottom opening, and
wherein the lower outer surface of the retainer further comprises a spherical surface configured to pivotably engage with the spherical seating surface to provide for pivotal motion between the receiver and the shank.

12. The pivotal bone anchor assembly of claim 1, wherein the channel of the receiver further comprises an open channel defined by a pair of upright arms extending upwardly from the base portion.

13. The pivotal bone anchor assembly of claim 12 and further comprising the longitudinal connecting member and the closure, wherein the closure is configured for positioning entirely within the open channel of the receiver above the longitudinal connecting member and in engagement with the helically wound guide and advance structure to apply a downward pressure to a top of the longitudinal connecting member, so as to secure the longitudinal connecting member to the bone of the patient.

14. A pivotal bone anchor assembly for securing a longitudinal connecting member to a bone of a patient via a closure, the pivotal bone anchor assembly comprising:
a receiver comprising a base portion defining a lower portion of a central bore centered on a vertical centerline axis and communicating with a bottom surface of the receiver through a bottom opening, and a pair of upstanding arms integral with the base portion defining a channel configured to receive the longitudinal connecting member, the central bore extending upward through the channel to tops of the upstanding arms and including a discontinuous helically wound thread form adjacent the tops of the upstanding arms and threadably engageable with the closure, at least one non-threaded downward-facing surface below the helically wound thread form, and a spherical seating surface adjacent the bottom opening;
a shank comprising a head portion with a lower spherical surface and an upper spherical surface and an anchor portion opposite the head portion configured for attachment to the bone, the head portion configured for positioning within the central bore with the lower spherical surface pivotally engageable with the spherical seating surface of the receiver and the shank extending downwardly through the bottom opening; and
a compression insert having a central opening, an upward facing surface configured to receive the longitudinal connecting member, a downward-facing spherical surface configured to directly engage the spherical upper surface of the head portion of the shank, and at least one horizontally extending notch formed into an upper portion of the compression insert to define at least one resiliently downwardly compressible structure extending over the at least one notch and having an upper engagement surface,
wherein the compression insert is positionable into the central bore of the receiver above the head portion of the shank, with the upper engagement surface of the at least one resiliently downwardly compressible structure in overlapping engagement with the at least one downward-facing surface of the central bore, so as to apply a resilient biasing frictional force onto the head portion of the shank prior to locking the assembly with the closure.

15. The pivotal bone anchor assembly of claim 14,
wherein the upper portion of the compression insert further comprises a pair of insert arms extending upward from the lower insert portion, and
wherein the upward facing surface of the compression insert further comprises an upwardly-open partial cylindrical surface extending between the pair of insert arms.

16. The pivotal bone anchor assembly of claim 15, wherein the compression insert is configured for positioning into the central bore of the receiver in a first position and then for rotation about the vertical centerline axis toward a second position to align the partial cylindrical surface with the channel of the receiver, with the upper engagement surface of the at least one resiliently downwardly compressible structure being rotated into engagement with the downward-facing surface of the central bore.

17. The pivotal bone anchor assembly of claim 16, further comprising at least one inner pocket formed into the central bore of the receiver between the at least one downward facing surface and the bottom opening and at least one protuberant interference structure projecting radially outward from a side of the compression insert,
wherein the at least one inner pocket is configured to receive the at least one protuberant interference structure upon rotation of the compression insert about the vertical centerline axis into the second position so as to inhibit further rotation of the compression insert with respect to the receiver in at least one direction.

18. The pivotal bone anchor assembly of claim 14, wherein the compression insert is downloadable into the central bore through the channel of the receiver.

19. The pivotal bone anchor assembly of claim 14, wherein the head portion of the shank is uploadable into the lower portion of the central bore through the bottom opening of the receiver.

20. The pivotal bone anchor assembly of claim 14 and further comprising a retainer configured for positioning within the lower portion of the central bore and for capturing the head portion of the shank within the base portion of the receiver.

21. The pivotal bone anchor assembly of claim 20, where the retainer is positionable within the lower portion of the central bore prior to the head portion of the shank.

22. A method of assembling a pivotal bone anchor assembly configured to secure a longitudinal connecting member to a bone of a patient with a closure, the method comprising:
positioning a compression insert into a central bore of a receiver,
the receiver comprising a base portion defining a lower portion of the central bore centered about a vertical centerline axis and communicating with a bottom surface of the base portion through a bottom opening, and an upper portion defining a channel configured to receive the longitudinal connecting member, the central bore extending upward from the bottom opening through the channel to a top of the upper portion and including a helically wound guide and advance structure adjacent the top of the upper portion, an integral non-threaded downward-facing surface below the helically wound guide and advance structure, and a support surface adjacent the bottom opening,
the compression insert comprising a lower insert portion defining a center opening and an upper insert portion having at least one horizontal notch formed therein to define at least one resiliently downwardly compressible structure extending over the at least one notch, with the at least one resiliently downwardly compressible structure being engageable with the downward-facing surface in the central bore of the receiver; and
positioning a head portion of a shank into the lower portion of the central bore of the receiver, the shank comprising the head portion and an anchor portion opposite the head portion configured for attachment to the bone,
wherein when the head portion of the shank and the compression insert are positioned together in the central bore of the receiver, the engagement between the at least one resiliently downwardly compressible structure and the downward-facing surface is configured to provide an axially directed resilient biasing force for a pre-lock friction fit of the pivotal bone anchor assembly prior to securing the longitudinal connecting member in the channel with the closure.

23. The method of claim 22,
wherein the compression insert further comprises an upper partial cylindrical surface alignable with the channel of the receiver and configured to receive the longitudinal connecting member, and
wherein positioning the compression insert into the central bore of the receiver further comprises rotating the compression insert about the vertical centerline axis from a first position in which the upper partial cylindrical surface is non-aligned with the channel toward a second position in which the upper partial cylindrical surface is aligned with the channel, and with the at least one resiliently downwardly compressible structure being rotated into engagement with the downward-facing surface of the central bore.

24. The method of claim 23, further comprising at least one inner pocket formed into the central bore of the receiver between the at least one downward: facing surface and the bottom opening and at least one protuberant interference structure projecting radially outward from a side of the compression insert,
wherein rotating the compression insert about the vertical centerline axis from the first position toward the second position further comprises rotating the at least one protuberant interference structure into the at least one inner pocket so as to inhibit further rotation of the compression insert with respect to the receiver in at least one direction.

25. The method of claim 22, further comprising positioning a retainer into the lower portion of the central bore of the receiver, the retainer having a lower outer surface configured to engage the seating surface of the axial bore and an inner surface configured to capture and hold the head portion of the shank within the base portion of the receiver.

26. The method of claim 25, further comprising positioning the retainer into the lower portion of the central bore prior to the head portion of the shank.

27. The method of claim 25, wherein positioning the head portion of the shank into the lower portion of the central bore further comprises uploading the head portion of the shank through the bottom opening.

* * * * *